United States Patent
Wang

(10) Patent No.: US 11,999,855 B2
(45) Date of Patent: Jun. 4, 2024

(54) FLUORESCENT DYE MOLECULES HAVING HYDROPHILICITY AND HYDROPHOBICITY FOR TRACER APPLICATIONS

(71) Applicant: Saudi Arabian Oil Company, Dhahran (SA)

(72) Inventor: Wei Wang, Cambridge, MA (US)

(73) Assignee: Saudi Arabian Oil Company, Dhahran (SA)

( * ) Notice: Subject to any disclaimer, the term of this patent is extended or adjusted under 35 U.S.C. 154(b) by 177 days.

(21) Appl. No.: 17/548,858

(22) Filed: Dec. 13, 2021

(65) Prior Publication Data

US 2023/0183488 A1 Jun. 15, 2023

(51) Int. Cl.
| | |
|---|---|
| C09B 11/24 | (2006.01) |
| C09B 11/08 | (2006.01) |
| G01N 21/64 | (2006.01) |
| G01N 33/24 | (2006.01) |

(52) U.S. Cl.
CPC .............. *C09B 11/24* (2013.01); *G01N 21/64* (2013.01); *G01N 33/24* (2013.01); *Y10T 436/13* (2015.01)

(58) Field of Classification Search
CPC .. G01N 33/24; G01N 33/2823; Y10T 436/13; C09B 11/24; C09B 11/08
See application file for complete search history.

(56) References Cited

U.S. PATENT DOCUMENTS

| | | | |
|---|---|---|---|
| 1,910,489 A | 5/1933 | Lubs et al. | |
| 2,033,949 A | 3/1936 | Lubs et al. | |
| 2,051,218 A | 8/1936 | Magoun et al. | |
| 2,061,243 A | 11/1936 | Lubs et al. | |
| 2,086,822 A | 7/1937 | Schubert et al. | |
| 2,339,621 A | 1/1944 | D'Alelio et al. | |

(Continued)

FOREIGN PATENT DOCUMENTS

| | | |
|---|---|---|
| EP | 0171978 | 11/1990 |
| EP | 1721603 | 11/2006 |

(Continued)

OTHER PUBLICATIONS

Okuno, Y. et al. "Thermoresponsive Carbohydrate-b-Polypeptoid Polymer Vesicles with Selective Solute Permeability and Permeable Factors for Solutes," Biomacromolecules 2021, 22, 7, 3099-3106; Jun. 24, 2021; including Supporting information (Year: 2021).*

(Continued)

*Primary Examiner* — Jennifer Wecker
*Assistant Examiner* — Michelle Adams
(74) *Attorney, Agent, or Firm* — Fish & Richardson P.C.

(57) ABSTRACT

Functionalized fluorescent tracers, methods of making the tracers, and methods of using the tracers are provided. In some implementations, the fluorescent tracers include a functionalized fluorescent dye. The functionalized fluorescent dye includes an isothiocyanate-containing dye functionalized with a functional group that includes a primary amine. In some implementations, a method of tracing fluid flow in a subterranean formation includes mixing the functionalized fluorescent tracer into a fluid, flowing the tracer fluid into a subterranean formation, recovering a sample from a subterranean formation, and analyzing the sample for a fluorescent signal and a barcode functional group.

17 Claims, 6 Drawing Sheets

(56) References Cited

U.S. PATENT DOCUMENTS

| | | |
|---|---|---|
| 2,390,848 A | 12/1945 | Richter |
| 2,455,894 A | 12/1948 | Lecher et al. |
| 2,479,498 A | 8/1949 | Lecher et al. |
| 2,885,421 A | 5/1959 | Spiegler |
| 3,086,962 A | 4/1963 | Mottus |
| 3,103,467 A | 9/1963 | Beaver |
| 3,238,176 A | 3/1966 | Brooks et al. |
| 3,241,971 A | 3/1966 | Kitze |
| 3,281,446 A | 10/1966 | Manning |
| 3,287,136 A | 11/1966 | McBride |
| 3,301,895 A | 1/1967 | Sayigh et al. |
| 3,637,785 A | 1/1972 | Smith et al. |
| 3,637,787 A | 1/1972 | Rasschaert |
| 3,654,214 A | 4/1972 | Beckman |
| 3,655,533 A | 4/1972 | Page |
| 3,953,506 A | 4/1976 | Spicer et al. |
| 3,953,606 A | 4/1976 | Spicer et al. |
| 4,148,799 A | 4/1979 | Enders |
| 4,461,821 A | 7/1984 | Sano et al. |
| 4,772,563 A | 9/1988 | Evangelista et al. |
| 4,921,939 A | 5/1990 | Nofre et al. |
| 5,124,268 A | 6/1992 | Dakubu |
| 5,168,927 A | 12/1992 | Stegenneier |
| 5,498,502 A | 3/1996 | Muramoto et al. |
| 5,677,120 A | 10/1997 | Lushington et al. |
| 6,250,848 B1 | 6/2001 | Moridis et al. |
| 6,331,436 B1 | 12/2001 | Richardson et al. |
| 6,590,647 B2 | 7/2003 | Stephenson |
| 6,691,780 B2 | 2/2004 | Nguyen et al. |
| 7,032,662 B2 | 4/2006 | Malone |
| 7,281,435 B2 | 10/2007 | Sale et al. |
| 7,485,471 B1 | 2/2009 | Sun et al. |
| 7,588,827 B2 | 9/2009 | Nie et al. |
| 7,861,601 B2 | 1/2011 | Sale et al. |
| 7,879,625 B1 | 2/2011 | Boss |
| 8,269,501 B2 | 9/2012 | Schmidt et al. |
| 8,337,783 B2 | 12/2012 | Locascio et al. |
| 8,627,902 B2 | 1/2014 | Hammer |
| 8,638,104 B2 | 1/2014 | Barber et al. |
| 8,877,954 B2 | 11/2014 | Giesenberg et al. |
| 9,034,920 B2 | 5/2015 | Lam et al. |
| 9,080,097 B2 | 7/2015 | Gupta et al. |
| 9,133,709 B2 | 9/2015 | Huh et al. |
| 9,322,056 B2 | 4/2016 | McCann et al. |
| 9,366,099 B2 | 6/2016 | Ly |
| 9,594,070 B2 | 3/2017 | Rule et al. |
| 10,273,399 B2 | 4/2019 | Cox |
| 10,308,865 B2 | 6/2019 | Cox |
| 10,308,895 B2 | 6/2019 | Vidal et al. |
| 10,400,159 B2 | 9/2019 | Gupta |
| 10,487,259 B2 | 11/2019 | Cox |
| 10,927,292 B2 | 2/2021 | Borrell et al. |
| 10,961,443 B2 | 3/2021 | Zhao |
| 10,961,445 B2 | 3/2021 | Ogle et al. |
| 2003/0220204 A1 | 11/2003 | Baran et al. |
| 2004/0108110 A1 | 6/2004 | Zupanick et al. |
| 2005/0252286 A1 | 11/2005 | Ibrahim et al. |
| 2006/0105052 A1 | 5/2006 | Acar et al. |
| 2007/0114030 A1 | 5/2007 | Todd et al. |
| 2008/0110253 A1 | 5/2008 | Stephenson et al. |
| 2008/0111064 A1 | 5/2008 | Andrews et al. |
| 2009/0087911 A1 | 4/2009 | Rogerio |
| 2009/0087912 A1 | 4/2009 | Ramos et al. |
| 2009/0248309 A1 | 10/2009 | Nelville et al. |
| 2009/0277625 A1 | 11/2009 | Bai et al. |
| 2010/0049625 A1 | 2/2010 | Biebesheimer et al. |
| 2010/0092865 A1 | 4/2010 | Kanno et al. |
| 2010/0224823 A1 | 9/2010 | Yin et al. |
| 2010/0307745 A1 | 12/2010 | Lafitte et al. |
| 2011/0012331 A1 | 1/2011 | Kim |
| 2011/0030949 A1 | 2/2011 | Weaver et al. |
| 2011/0207231 A1 | 8/2011 | Natan et al. |
| 2011/0239754 A1 | 10/2011 | Dyer et al. |
| 2011/0257887 A1 | 10/2011 | Cooper et al. |
| 2011/0260051 A1 | 10/2011 | Preudhomme et al. |
| 2011/0275061 A1 | 11/2011 | Weidemaier et al. |
| 2012/0062886 A1 | 3/2012 | Piotti et al. |
| 2012/0115128 A1 | 5/2012 | Miller |
| 2012/0135080 A1 | 5/2012 | Bromberg et al. |
| 2012/0193578 A1 | 8/2012 | Pan et al. |
| 2012/0225274 A1 | 9/2012 | Ishikawa et al. |
| 2012/0257199 A1 | 10/2012 | Liu et al. |
| 2012/0261617 A1 | 10/2012 | Pan et al. |
| 2012/0325465 A1 | 12/2012 | Hammer et al. |
| 2013/0017610 A1 | 1/2013 | Roberts et al. |
| 2013/0040292 A1 | 2/2013 | Lopez et al. |
| 2013/0084643 A1 | 4/2013 | Commarieu et al. |
| 2013/0087329 A1 | 4/2013 | Hewitt et al. |
| 2013/0109261 A1 | 5/2013 | Koene |
| 2013/0244914 A1 | 9/2013 | Wu et al. |
| 2013/0259808 A1 | 10/2013 | Chen et al. |
| 2013/0296453 A1 | 11/2013 | Giesenberg et al. |
| 2013/0312970 A1 | 11/2013 | Lafitte et al. |
| 2013/0341030 A1 | 12/2013 | Brannon et al. |
| 2014/0060832 A1 | 3/2014 | Mahoney et al. |
| 2014/0077121 A1 | 3/2014 | Sun et al. |
| 2014/0120627 A1 | 5/2014 | Rubino et al. |
| 2014/0124196 A1 | 5/2014 | Sunde et al. |
| 2014/0186939 A1 | 7/2014 | Peterman et al. |
| 2014/0190700 A1 | 7/2014 | Tang et al. |
| 2014/0231077 A1 | 8/2014 | Rivero et al. |
| 2014/0260694 A1 | 9/2014 | Szlendak |
| 2014/0323363 A1 | 10/2014 | Perriat |
| 2014/0360973 A1 | 12/2014 | Yin et al. |
| 2015/0013983 A1 | 1/2015 | Alwattari |
| 2015/0038347 A1 | 2/2015 | Johnson et al. |
| 2015/0050741 A1 | 2/2015 | Tour et al. |
| 2015/0079270 A1 | 3/2015 | Wang et al. |
| 2015/0118501 A1 | 4/2015 | Lu |
| 2015/0132543 A1 | 5/2015 | Nouzille et al. |
| 2015/0159079 A1 | 6/2015 | Huh et al. |
| 2015/0218379 A1* | 8/2015 | Gee .......... C09B 11/24 436/163 |
| 2015/0232747 A1 | 8/2015 | Kanj et al. |
| 2015/0268370 A1 | 9/2015 | Johnston et al. |
| 2015/0368547 A1 | 12/2015 | Lesko et al. |
| 2015/0376493 A1 | 12/2015 | Huh et al. |
| 2016/0003040 A1 | 1/2016 | Jessheim et al. |
| 2016/0040514 A1 | 2/2016 | Rahmani et al. |
| 2016/0083641 A1 | 3/2016 | Gamage |
| 2016/0097750 A1 | 4/2016 | Van Herzen et al. |
| 2016/0215030 A1 | 7/2016 | Bressner |
| 2016/0264846 A1 | 9/2016 | Bennetzen et al. |
| 2016/0304934 A1 | 10/2016 | Matsuno |
| 2017/0022804 A1 | 1/2017 | Gupta et al. |
| 2017/0059668 A1 | 3/2017 | Chang et al. |
| 2017/0199124 A1 | 7/2017 | Bolduc et al. |
| 2017/0350236 A1 | 12/2017 | Shen et al. |
| 2017/0361376 A1 | 12/2017 | Murugesan et al. |
| 2018/0171782 A1 | 6/2018 | Cox et al. |
| 2018/0275114 A1 | 9/2018 | Kosynkin et al. |
| 2019/0118265 A1 | 4/2019 | Nie et al. |
| 2019/0218907 A1 | 7/2019 | Ow et al. |
| 2019/0226326 A1 | 7/2019 | Ow et al. |
| 2019/0368336 A1 | 12/2019 | Hammond et al. |
| 2019/0382648 A1 | 12/2019 | Murugesan et al. |
| 2021/0025858 A1 | 1/2021 | Ow et al. |
| 2023/0141596 A1 | 5/2023 | Wang et al. |
| 2023/0141819 A1 | 5/2023 | Wang et al. |
| 2023/0144199 A1 | 5/2023 | Wang et al. |
| 2023/0182110 A1 | 6/2023 | Wang et al. |
| 2023/0235218 A1 | 7/2023 | Wang |

FOREIGN PATENT DOCUMENTS

| | | |
|---|---|---|
| EP | 2040075 | 3/2009 |
| EP | 2480625 | 4/2013 |
| EP | 2480626 | 4/2013 |
| GB | 2489714 | 10/2012 |
| JP | 2005524849 | 8/2005 |
| JP | 2007514169 | 5/2007 |
| JP | 2008505259 | 2/2008 |
| JP | 2008524602 | 7/2008 |
| JP | 2009535060 | 10/2009 |

(56) References Cited

FOREIGN PATENT DOCUMENTS

| | | |
|---|---|---|
| JP | 2009540326 | 11/2009 |
| JP | 2015523073 | 8/2015 |
| WO | WO 2010138914 | 12/2010 |
| WO | WO 2011035292 | 3/2011 |
| WO | WO 2011035294 | 3/2011 |
| WO | WO 2011063023 | 5/2011 |
| WO | WO 2012154332 | 11/2012 |
| WO | WO 2012158478 | 11/2012 |
| WO | WO 2013142869 | 9/2013 |
| WO | WO 2014014919 | 1/2014 |
| WO | WO 2014066793 | 5/2014 |
| WO | WO 2014096495 | 6/2014 |
| WO | WO 2014207075 | 12/2014 |
| WO | WO 2015044446 | 4/2015 |
| WO | WO 2015058206 | 4/2015 |
| WO | WO 2015097116 | 7/2015 |
| WO | WO 2015200060 | 12/2015 |
| WO | WO 2016087397 | 6/2016 |
| WO | WO 2017011328 | 1/2017 |
| WO | WO 2017136641 | 8/2017 |
| WO | WO 2017164822 | 9/2017 |
| WO | WO 2018085504 | 5/2018 |
| WO | WO 2018175763 | 9/2018 |
| WO | WO 2021092328 | 5/2021 |

OTHER PUBLICATIONS

Seydack, M. et al. "trans-Stilbene Photochemistry Beyond 500 nm," Journal of Fluorescence, vol. 10, No. 3, 2000, 291-294. (Year: 2000).*

Kim, T.W. et al. "Molecular Tripods Showing Fluorescence Enhancement upon Binding to Streptavidin," Org. Lett., vol. 7, No. 1, 2005, 111-114, including Supporting information (Year: 2005).*

Lin, H.-J. et al. "Toward live-cell imaging of dopamine neurotransmission with fluorescent neurotransmitter analogues," Chem. Commun., 2015, 51, 14080-14083, including Electronic supplementary information (Year: 2015).*

Amendola et al, "The interaction of fluoride with fluorogenic ureas: an On/∧1-Off-On/∧2 response," Journal of the American Chemical Society, 2013, 135, 6345-6355, 11 pages.

Berry et al, "Fluorescent transmembrane anion transporters: shedding light on anionophoric activity in cells," Chemical Science, 2016, 7:5069-5077, 9 pages.

Byrne et al, "Urea and thiourea based anion receptors in solution and on polymer supports," Supramolecular Chemistry, 2018, 30:196-205, 10 pages.

Campbell et al, "p-Methoxyphenylisothiocyanate as a Reagent for the Identification of Amines," Proceedings of the Indiana Academy of Science, 1943, 53:119-121, 3 pages.

Cui et al, "Fluorescent investigation of the interactions between N-(p-chlorophenyl)-N'-(1-naphthyl) thiourea and serum albumin: Synchronous fluorescence determination of serum albumin," Analytica Chimica Acta, 2006, 571:175-183, 9 pages.

Dieke et al, "The acute toxicity of thioureas and related compounds to wild and domestic Norway rats," Journal of Pharmacology and Experimental Therapeutics, 1947, 90:260-270, 11 pages.

Dos Santos et al, "Selective fluorescent sensing of chloride," Supramolecular Chemistry, 2008, 20:407-418, 5 pages.

Dos Santos et al, "Synthesis, Structural and Photophysical Evaluations of Urea Based Fluorescent PET Sensors for Anions," Tetrahedron Letters, 2007, 48, 3135-3139, 13 pages.

Fesenko et al, "Different pathways in the reaction of N-(tosylmethyl)-substituted ureas, thioureas, and N'-cyanoguanidines with sodium cyanide. Synthesis of α-ureido nitriles, α-ureido amides, and hydantoin imino derivatives," Tetrahedron, 2020, 76(40), 18 pages.

French et al, "Alpha-naphthylisocyanate as a reagent for phenols for aliphatic amines/∧1," Journal of the American Chemical Society, 1926, 48:1736-1739, 4 pages.

Gomez et al, "Urea vs. thiourea in anion recognition," Organic & Biomolecular Chemistry, 2005, 3:1495-1500, 7 pages.

Hacker et al, "Aromatic 2-(Thio)ureidocarboxylic Acids As a New Family of Modulators of Multidrug Resistance-Associated Protein 1: Synthesis, Biological Evaluation, and Structure-Activity Relationships," Journal of Medicinal Chemistry, 2009, 52:4586-45, 10 pages.

Ikedu et al, "Kinetics of Hydrogen Bonding between Anthracene Urea Derivatives and Anions in the Excited State," The Journal of Physical Chemistry A, 2011, 115:8227-8233, 7 pages.

Kim et al, "Novel Solid-Phase Parallel Synthesis of N-Substituted-2-aminobenzo [d]thiazole Derivatives via Cyclization Reactions of 2-Iodophenyl Thiourea Intermediate Resin," ACS Combinatorial Science, 2013, 15, 29-40, 12 pages.

Kinsella et al, "Synthesis and NMR Binding Studies towards Rational Design of a Series of Electron-Withdrawing Diamide Receptors/Organocatalysts," European Journal of Organic Chemistry, 2011, 1125-1132, 42 pages.

Kwon et al, "Unique hydrogen bonds between 9-anthracenyl hydrogen and anions," Journal of Organic Chemistry, 2004, 69:5155-5157, 3 pages.

Li et al, "A new and efficient solid state synthesis of diaryl thioureas," Synthetic Communications, 2001, 31:781-785, 5 pages.

Lin et al, "A new selective colorimetric and fluorescent sensor for Hg2+ and Cu2+ based on a thiourea featuring a pyrene unit," Talanta, 2010, 81:1209-1215, 7 pages.

Muller et al, "N,N'-Disubstituted guanidine high potency sweetners," Journal of Medicinal Chemistry, 1992, 35:740-743, 4 pages.

Nishizawa et al, "Anion recognition by a pyrene derivative with a thiourea function," Analytical Sciences, 1997, 13, supplement, 485-488, 4 pages.

Rahman et al, "Thiourea Derivatives, Simple in Structure but Efficient Enzyme Inhibitors and Mercury Sensors," Molecules, 2021, 26, 16 pages.

Ros-Lis et al, "Signaling Mechanisms in Anion-Responsive Push-Pull Chromophores: The Hydrogen-Bonding, Deprotonation and Anion-Exchange Chemistry of Functionalized Azo Dyes," European Journal of Organic Chemistry 2007, 2449-2458, 10 pages.

Sah, "p-bromo phenyl isothiocyanate as a reagent for the identification of aromatic amines," Journal of the Chinese Chemical Society, 1934, 2:225-228, 5 pages.

Suter et al, "Alpha-Naphthyl Isothiocyanate as a Reagent for Primary and Secondary Aliphatic Amines," Journal of the American Chemical Society, Jun. 1933, 55:2497-2499, 3 pages.

Wu et al, "Synthesis and biological evaluation of novel anti-hepatitis C virus (HCV) agents: 2-hydroxylphenethyl sulfanyl-oxopyrimidines," Medicinal Chemistry Research, 2017, 26:1388-1396, 9 pages.

Xie et al, "Study on host-guest complexation of anions based on a tripodal naphthylurea derivatives," Journal of the Chemical Society, Perkin Transactions 2, 1999, 2:2751-2754, 5 pages.

Gunnlaugsson et al., "Design, synthesis and photophysical studies of simple fluorescent anion PET sensors using charge neutral thiourea receptors," Organic & Biomolecular Chemistry, 2004, 2:1856-1863, 8 pages.

U.S. Appl. No. 17/454,176, filed Nov. 9, 2021, Wang et al.
U.S. Appl. No. 17/454,181, filed Nov. 9, 2021, Wang et al.
U.S. Appl. No. 17/522,437, filed Nov. 9, 2021, Wang et al.
U.S. Appl. No. 17/522,445, filed Nov. 9, 2021, Wang et al.
U.S. Appl. No. 17/548,837, filed Dec. 13, 2021, Wang.
U.S. Appl. No. 17/549,062, filed Dec. 13, 2021, Wang.
U.S. Appl. No. 17/643,931, filed Dec. 13, 2021, Wang.

Agenet et al., "SPE 157019: Fluorescent Nanobeads: a First Step Toward Intelligent Water Tracers" Society of Petroleum Engineers, SPE International Oilfield Nanotechnology conference, Jun. 12-14, 2012, 13 pages.

Alley et al., "Analysis of Polychlonnated Biphenyls in Fatty Biological Matrixes by On-Line Supercritical Fluid Extraction and Supercritical Fluid Cleanup." Journal of AOAC International 78.4, Jul. 1995, 1051-1054, 4 pages.

Anisimov, "SPE 118862: The Use of Tracers for Reservoir Characterization" Society of petroleum Engineers (SPE), presented at SPE Middle East Oil and Gas Show and Conference, Mar. 15-18, 2009, 8 pages.

(56) References Cited

OTHER PUBLICATIONS

Armelao et al., "Design of luminescent lanthanide complexes: From molecules to highly efficient photo-emitting materials" Coordination Chemistry Reviews, vol. 254, 5-6, Mar. 2010, 19 pages.

Aslan et al., "Fluorescent Core-Shell AG@SiO$_2$ Nanocomposites for Metal-Enhanced Fluorescence and Single Nanoparticle Sensing Platforms" Jan. 19, 2007, 2 pages.

Badgett et al., "Totalsynthese eines Neobetanidin-Derivates und des Neobetenamins" Helvetica Chimica Acta, 1970, 53(2): 433-448, 16 pages (English Abstract).

Bagaria et al., "Iron Oxide Nanoparticles Grafted with Sulfonated Copolymers are Stable in Concentrated Brine at Elevated Temperatures and Weakly Adsorb on Silica" ACS Applied Materials & Interfaces, vol. 5, No. 8, Mar. 25, 2013, 3329-3339, 11 pages.

Bala et al., "Interaction of Different Metal Ions with Carboxylic Acid Group: A Quantitative Study" The Journal of Physical Chemistry A, vol. 111, No. 28, Jun. 2007, 6183-6190, 8 pages.

Bao et al., "Luminescence properties of the co-luminescence groups of Sm-La-pyridyl carboxylic acids" Journal of Rare Earths, 30(4), Apr. 2012, 320-324, 5 pages.

Blachier et al., "Adsorption of polyamine on clay minerals" Journal of Colloid and Interface Science, 336, Aug. 2009, 599-606, 8 pages.

Borrini et al., "Water Soluble PDCA Derivatives for Selective Ln(III)/An(III) and Am(III)/Cm(III) Separation" Solvent Extraction and Ion Exchange, 33(3), Oct. 2014, 224-235, 30 pages.

Brichart et al., "The Use of Fluorescent Tracers for Inhibitor Concentration Monitoring Useful for Scale Inhibitor" International Petroleum Technology Conference, IPTC-17933-MS, presented at the International Petroleum Technology Conference held in Kuala Lumpur, Malaysia, Dec. 10-12, 2014, 8 pages.

Bunzil et al., "Taking advantage of luminescent lanthanide ions" Chemical Society Reviews, Dec. 2005, 29 pages.

Cao et al., "Solute reactive tracers for hydrogeological applications: A short review and future prospects." Water 12.3, Mar. 2020, 21 pages.

Chang et al., "Magnetic SERS Composite Nanoparticles for Microfluidic Detection" 251st ACE National Meeting, Mar. 13-17, 2016, 1 page.

Chemspider.com [online], "Structure Search" Mar. 2008, [retrieved on Feb. 15, 2022], retrieved from : URL <http://www.chemspider.com/structuresearch.aspx>, 1 page.

Chen et al., "Aggregation Kinetics of Alginate-Coated Hematite Nanoparticles in Monovalent and Divalent Electrolytes" Environmental Science & Technology, vol. 40, No. 5, Mar. 2006, 1516-1523, 9 pages.

Chen et al., "Analysis of the solution conformations of T4 lysozyme by paramagnetic NMR spectroscopy" Physical Chemistry Chemical Physics, 2016, 18(8), 5850-5859, 10 pages.

Chen et al., "Impact of Irreversible Retention on Tracer Deployments; Constraining Novel Material Deployments" SPE 188890-MS, in SPE Abu Dhabi International Petroleum Exhibition and Conference, Society of Petroleum Engineers, Nov. 2017, 8 pages.

Chen et al., "Improved Reservoir History Matching and Prudction Optimization with Tracer Data" SPE 191523-MS, in SPE Annual Technical Conference and Exhibition, Society of Petroleum Engineers, Sep. 2018, 15 pages.

Chen et al., "Upconversion Nanoparticles: Design, Nanochemistry, and Applications in Theranostics" Chem. Rev, 114(10), Mar. 2014, 5161-5214, 54 pages.

Chen et al., "FITC functionalized magnetic core-shell Fe$_3$O$_4$/Ag hybrid nanoparticle for selective determination of molecular biothiols" Elsevier Ltd., Dec. 2013, 7 pages.

Chen et al.; "Hydration Repulsion between Carbohydrate Surfaces Mediated by Temperature and Specific Ions" Scientific Reports, vol. 6, Jun. 23, 2016, 10 pages.

Cheraghian, "Application of nano-particles of clay to improve drilling fluid" Int. J. Nanosci. Nanotechnol., 13, Jun. 2017, 177-186, 10 pages.

Chuang et al., "Ultra-sensitive in-situ detection of novel near-infrared persistent luminescent tracer nanoagents in crude oil-water mixtures" a natureresearch journal, Scientific Reports, Jun. 15, 2016, 5 pages.

Coates et al, "Enhancement of luminescence of europium(m) ions in water by use of synergistic chelation. Part 1.1 : 1 and 2 : 1 complexes" J. Chem. Soc, Perkin Trans., Jan. 1996, 1275-1282, 8 pages.

Cole et al.; "Polyethylene Glycol Modified, Cross-Linked Starch-Coated Iron Oxide Nanoparticles for Enhanced Magnetic tumor Targeting" Biomaterials, vol. 32, No. 8, Mar. 1, 2011, 2183-2193, 11 pages.

Cox et al., "Pyrolyzable Nanoparticle Tracers for Environmental Interrogation and Monitoring" ACS Appl. Mater. Interfaces, 2017, 9(15), 13111-13120, 10 pages.

Cubillos et al., "SPE 174394-MS: The Value of Inter-well and Single Well Tracer Technology for De-Risking and Optimizing a CEOR Process-Caracara Field Case" Society of Petroleum Engineers (SPE), presented at EUROPEC 2015, Jun. 1-4, 2015, 19 pages.

Das et al., "Molecular Fluorescence, Phosphorescence, and Chemiluminescence Spectrometry" Analytical Chemistry, Nov. 3, 2011, 29 pages.

Deans, "SPE 7076: Using Chemical Tracers To Measure Fractional Flow And Saturation In-Situ" Society of Petroleum Engineers (SPE), presented at SPE Symposium on improved Methods of Oil Recovery, Apr. 16-17, 1978, 10 pages.

Deschamps et al., "Drilling to the Extreme: the Micro-Coring Bit Concept" IADC/SPE 115187, presented at the IADC/SPE Asai Pacific Drilling Technology Conference and Exhibition, Aug. 25-27, 2008, 12 pages.

Desmette et al., "Drilling Hard and Abrasive Rock Efficiently, or Generating Quality Cuttings? You No Longer Have to Choose . . . " SPE 116554, Society of Petroleum Engineers, 2008 SPE Annual Technical Conference and Exhibition, Sep. 21-24, 2008, 19 pages.

Du et al., "SPE 93140: Interwell Tracer Tests: Lessons Learnted from past Field Studies" Society of Petroleum Engineers (SPE), presented at SPE Asia Pacific Oil and Gas Conference and Exhibition, Apr. 5-7, 2005, 9 pages.

Dugstad, "Chapter 6: Well-to-well tracer tests" in Petroleum Engineering Handbook, 2007, 651-683, 31 pages.

Dung et al., "Structural and magnetic properties of starch coated magnetite nanoparticles" Journal of Experimental Nanoscience, 4, Sep. 2009, 259-267, 9 pages.

Edwards et al., "Extending the distance range accessed with continuous wave EPR with Gd3+ spin probes at high magnetic fields" Physical Chemistry Chemical Physics, 15(27), 2013, 11313-11326, 14 pages.

El-Aneed et al., "Mass Spectrometry, Review of the Basics: Electrospray, MALDI, and Commonly Used Mass Analyzers" Applied Spectroscopy Reviews, Mar. 16, 2009, 22 pages.

Fichtel et al., "A highly sensitive HPLC method for determination of nanomolar concentrations of dipicolinic acid, a characteristic constituent of bacterial endospores" Journal of Microbiological Methods, 2007, 70, 319-327, 9 pages.

Flury et al., "Dyes as tracers for vadose zone hydrology." Reviews of Geophysics 41.1, Mar. 2003, 37 pages.

Freeze and Cherry, "Chapter 9: Groundwater Contamination" in Groundwater, Englewood Cliffs, NJ: Prentice-Hall, Inc., 1979, 80 pages.

Galdiga and Greibrokk, "Ultra-trace determination of flurinated aromatic carboxylic acids in aqueous reservoir fluids using solid-phase extraction in combination with gas chromatography-mass spectrometry" Journal of Chromatography, vol. 793, Issue 2, Apr. 1997, 297-306, 10 pages.

Gao et al., "A Surface Functional Monomer-Directing Strategy for Highly Dense Imprinting of TNT at Surface of Silica Nanoparticles" Journal of American Chemical Society, vol. 129, No. 25, Jun. 2007, 7859-7866, 8 pages.

Gardiner et al., "Practical Raman Spectroscopy" Springer-Verlag, 1989, 9 pages.

(56) References Cited

OTHER PUBLICATIONS

Ge et al., "Fluorescence modified chitosan coated magnetic nanoparticles for high-efficienct cellular imaging" Nanoscale Res. Lett, 4, Jan. 2009, 287-295, 9 pages.
George et al., "Modified Dipicolinic Acid Ligands for Sensitation and Europium (III) Luminescence" Inorganic Chemistry, vol. 45, No. 4, Feb. 1, 2006, 6 pages.
Georgi, et al., "Advances in Cuttings Collection and Analysis" SPWLA 34th Annual Logging Symposium, Jun. 13-16, 1993, 20 pages.
Gordon-Grossman et al., "W-Band pulse EPR distance measurements in peptides using Gd3+-dipicolinic acid derivatives as spin labels" Physical Chemistry Chemical Physics, 13(22), 2011, 10771-10780, 10 pages.
Grutzke et al., "Heptacoordinate Heteroleptic Salan (ONNO) and Thiosalan (OSSO) Titanium(IV) Complexes: Investigation of Stability and Cytotoxicity" Inorganic Chemistry 54(14), Jul. 2015, 6697-6706, 10 pages.
Hagoot, "The response of interwell tracer tests in watered-out reservoirs" SPE 11131-MS, in SPE Annual Technical Conference and Exhibition, Society of Petroleum Engineers, Jan. 1982, 21 pages.
Han et al., "Application of Silver-Coated Magnetic Microspheres to a SERS-Based Optofluidic Sensor" The Journal of Physical Chemistry (JPCC), Mar. 7, 2011, 7 pages.
Hardy et al., "A novel fluorescent tracer for real-time tracing of clay transport over soil surfaces" Catena, 141, Jun. 2016, 39-45, 7 pages.
He et al., "Luminescent Europium Chelates Synthesis and Fluorescence Properties" Sensors and Materials (2007), 19(2), 123-132, 10 pages.
Hindle et al., "Dipicolinic acid (DPA) assay revisited and appraised for spore detection" Analyst, 1999, 124: 1599-1604, 6 pages.
Hu et al., "Smart Liquid SERS Substrates based on $Fe_3O_4$/Au Nanoparticles with Reversibility Tunable Enhancement Factor for Practical Quantitative Detection" a natureresearch journal, Scientific Reports, Nov. 27, 2014, 10 pages.
Huseby et al., "Assessing EOR potential from partitioning tracer data" SPE 172808-MS, in SPE Middle East Oil and Gas Show and Conference, Society of Petroleum Engineers, Mar. 2015, 15 pages.
Huseby et al., "SPE-169183-MS: High Quality Flow Information from Tracer Data" Society of Petroleum Engineers (SPE), presented at the SPE Bergen One Day Seminar, Apr. 2, 2014, 9 pages.
Hutchins et al., "SPE-21049: Aqueous Tracers for Oilfield Applications" Society of Petroleum Engineers (SPE), presented at SPE International Symposium on Oilfield Chemistry, Feb. 20-22, 1991, 9 pages.
Invitrogen, "Fluorophores and Their Amine-Reactive Derivatives" Molecular Probs Handbook, A Guide to Fluorescent Probes and Labeling Technologies, 11th Edition, 2010, 88 pages.
Jenkins et al., "Ultratrace Determination of Selected Lanthanides by Luminescence Enhancement" Analytical Chemistry, vol. 68, No. 17, Jan. 1, 1996, 7 pages.
Jun et al., "Multifunctional Silver-Embedded Magnetic Nanoparticles as SERS Nanoprobes and Their Applications" Wiley-VCH Verlag GmbH& Co. KGaA, Weinheim, Jan. 4, 2010, 7 pages.
Kaushik et al., "Gd(III) and Mn(II) complexes for dynamic nuclear polarization: small molecular chelate polarizing agents and applications with site-directed spin labeling of proteins" Physical Chemistry Chemical Physics, 18(39), 2016, 27205-27218, 36 pages.
Khalil et al., "Organic dye for subsea flowline assessment." SPE International Symposium on Oilfield Chemistry. OnePetro, Feb. 1999, 7 pages.
Khan et al., "Optimizing waterflood management in a giant UAE carbonate oil field using simulation-based streamlines" SPE 171777-MS, in Abu Dhabi International Petroleum Exhibition and Conference, Society of Petroleum Engineers, Nov. 10-13, 2014, 9 pages.
Kneipp et al., "Single Molecule Detection Using Surface-Enhanced Raman Scattering (SERS)" Physical Review Letters, American Physical Society vol. 78, No. 9, Mar. 3, 1997, 4 pages.

Kornberger and Thiele, "Experiences with an Efficient Rate-Management Approach for the 8th Tortonian Reservoir in the Vienna Basin" SPE 166393-PA, SPE Reservoir Evaluation and Engineering, vol. 17, No. 2, May 2014, 12 pages.
Kosynkin and Alaskar, "Oil Industry First Interwell Trial of Reservoir Nanoagent Tracers" SPE 181551-MS, in SPE Annual Technical Conference and Exhibition, Society of Petroleum Engineers, Sep. 2016, 15 pages.
Kramer, "Water-Soluble Dendritic Architectures with Carbohydrate Shells for the Templation and Stabilization of Catalytically Active Metal Nanoparticles" published by ACS, Macromolecules, vol. 38, No. 20, Aug. 27, 2005, 8308-8315, 8 pages.
Labbe et al., "Development of metal-chelating inhibitors for the Class II fructose 1,6-bisphosphate (FBP) aldolase" Journal of Inorganic Biochemistry, 112, Jul. 2012, 49-58, 10 pages.
Lachowicz et al., "Biocompatible and fluorescent superparamagnetic iron oxide nanoparticles with superior magnetic properties coates with charged polysaccharide derivatives" Colloids and Surfaces B: Biointerfaces, 2017, 150, 402-407, 18 pages.
Larsen et al, "Efficient Synthesis of 4,7-Diamino Substituted 1,10-Phenanthroline-2,9-dicarboxamides" Organic Letters, vol. 13, No. 13, Jul. 2011, 3546-3548, 3 pages.
Li et al., "An amino-endcapped octadecylsilane silica-based mixed-mode stationary phase for the simultaneous separation of neutral and ionizable components in fixed-dose combinations." Analytical Methods Nov. 30, 2019, 3898-3909, 12 pages.
Li et al., "Long persistent phosphors-from fundamentals to applications" Chem. Soc. Rev., 45(8), Apr. 2016, 2090-2136, 48 pages.
Li et al., "Magic Angle Spinning NMR Structure Determination of Proteins from Pseudocontact Shifts" Journal of the American Chemical Society, 135(22), May 2013, 8294-8303, 10 pages.
Li et al., "Superparamagnetic Iron Oxide Nanoparticles as MRI contrast agents for Non-invasive Stem Cell Labeling and Tracking" Theranostics, Jul. 2013, 3(8):595-615, 21 pages.
Li et al., "Thiol-ene reaction: a versatile tool in site-specific labelling of proteins with chemically inert tags for paramagnetic NMR" Chemical Communications, Cambridge, United Kingdom, 48(21), 2704-2706, 2012, 18 pages, Supporting Information only.
Liu et al., "Photostimulated near-infrared persistent luminescence as a new optical read-out from Cr3+-doped LiGa5O8" Scientific Reports 3, Article 1554, Mar. 2013, 9 pages.
Liu et al., "Separation of polyethylene glycols and their fluorescein-labeled compounds depending on the hydrophobic interaction by high-performance liquid chromatography." Journal of Chromatography A 1129.1, Sep. 2006, 61-66, 6 pages.
Lomstein and Jorgensen, "Pre-column liquid chromatographic determination of dipicolinic acid from bacterial endospores" Limnology and Oceanography: Methods, Apr. 2012, 10:4, 227-233, 14 pages.
Mahdavi et al., "Preparation, Characterization, and Application of Polyacrylamide-Polystyrene/Bentonite Nanocomposite as an Effective Immobilizing Adsorbent for Remediation of Soil" Chemistry Select, Apr. 5, 2020, 4538-4547, 12 pages.
Mahmoudi et al., "Superparamagnetic iron oxide nanoparticles development surface modification and applications in chemotherapy" Advanced Drug Delivery Reviews, Jan. 2011, 63, 24-46, 23 pages.
Manna et al, "Complexation behavior of trivalent actinides and lanthanides with 1,10-phenanthroline-2,9-dicarboxylic acid based ligands: insight from density functional theory" Physical Chemistry Chemical Physics, vol. 14, No. 31, Jan. 2012, 11060-11069, 10 pages.
Marais, A., et al. "Time-Resolved Fluorescence for Real-Time Monitoring of Both Scale and Corrosion Inhibitors: A Game-Changing Technique" SPE International Oilfield Scale Conference and Exhibition. OnePetro, May 2016, 11 pages.
Marchetti et al., "Fluorous affinity chromatography for enrichment and determination of perfluoroalkyl substances" Annual Review of Analytical Chemistry vol. 84, Jul. 19, 2012, 8 pages.
Martinez et al., "Polysaccharide-based Nanoparticles for Controlled Release Formulations" The Delivery of Nanoparticles, Published May 2012, 185-222, 40 pages.
Martini et al., "How to Monitor Scale Inhibitor Squeeze using Simple TRF Tracers" Society of Petroleum Engineers, presented at

(56) References Cited

OTHER PUBLICATIONS the SPE International Symposium on Oilfield Chemistry held in the Woodlands, Texas, Apr. 13-15, 2015, 8 pages.

McWilliams et al., "Fluorescent surfactants from common dyes-rhodamine B and eosin Y." Pure and Applied Chemistry 92.2, Feb. 2020, 265-274, 15 pages.

Melton et al, "Complexes of Greatly Enhanced Thermodynamic Stability and Metal Ion Size-Based Selectivity, Formed by the Highly Preorganized Non-Macrocyclic Ligand 1,10-Phenanthroline-2,9-dicarboxylic Acid: A Thermodynamic and Crystallographic Study" Inorganic Chemistry vol. 45 No. 23, Jun. 2006, 9 pages.

Moyner et al., "The Application of Flow Diagnostics for Reservoir Management" Society of Petroleum Engineers (SPE), Apr. 2015, 18 pages.

Muller and Seubert, "Ultra trace determination of fluorobenzoic acids in tap and reservoir water using solid-phase extraction and gas chromatography-mass spectrometry" Journal of Chromatography A, 1260, Oct. 2012, 7 pages.

Nie et al., "Probing Single Molecules and Single Nanoparticles by Surface-Enhanced Raman Scattering" Science, vol. 275, No. 5303, Feb. 1997, 1102-1106, 6 pages.

Ogden et al, "Complexation of Am(III) and Nd(in) by 1,10-Phenanthroli ne-2,9-Di carboxylic Acid" Journal of Solution Chemistry, vol. 42, No. 1, pp. 211-225, 2013, 15 pages.

Ouali et al., "Analysis of Paramagnetic NMR Spectra of Triple-Helical Lanthanide Complexes with 2,6-Dipicolinic Acid Revisited: A New Assignment of Structural Changes and Crystal-Field Effects 25 Years Later" Inorganic Chemistry, 41(6), Feb. 2002, 1436-1445, 10 pages.

Pallenberg et al. "Synthesis and Characterization of Some Copper(I) Phenanthroline Complexes" Inorg. Chem. 1995, 34, 2833-2840, 8 pages.

Park et al., "Application of montmorillonite in bentonite as a pharmaceutical excipient in drug delivery systems" Journal of Pharmaceutical Investigation, 46, May 2016, 363-375, 13 pages.

Parker and Williams, "Getting excited about lanthanide complexation chemistry" Journal of the Chemical Society, Dalton Transactions, vol. 18, 1996, 16 pages.

Parker et al., "Being excited by lanthanide coordination complexes: aqua species, chirality, excited-state chemistry, and exchange dynamics" Chemical Reviews, vol. 102, Issue 6, May 2002, 34 pages.

Petoud et al., "Brilliant SM, Eu, Tb, and Dy Chiral Lanthanide Complexes with Strong Circularly Polarized Luminescence" Journal fo the American Chemical Society (JACS), Dec. 15, 2006, 7 pages.

Potapov et al., "Nanometer-Scale Distance Measurements in Proteins Using Gd3+ Spin Labeling" Journal of the American Chemical Society, 132(26), Jun. 2010, 9040-9048, 9 pages.

Qianming et al., "Bspda Synthesis and its Europium (III) Complexes' Fluorescence" Chemical Industry Times, Jul. 2005, 19(7): 38-41, 4 pages (English Abstract).

Rashdan et al., "Effect of the preparation route, PEG and annealing on the phase stability of Fe3O4 nanoparticles and their magnetic properties" Journal of Experimental Nanoscience, vol. 8, No. 2, 2013, 210-222, 13 pages.

Rovani, "Enhanced Oil Recovery: Aqueous Flow Tracer Measurement" WRI-09-R002, OSTI.Gov, Technical Report, U.S. Department of Energy, Feb. 2009, 1-18, 25 pages.

Rowan et al., "Dynamic Covalent Chemistry" Angewante Chemie International Edition, Mar. 15, 2002, 55 pages.

Sabbatini et al., "Luminescent lanthanide complexes as photochemical supramolecular devices" Coordination Chemistry Reviews, vol. 123, issue 1-2, Feb. 1993, 28 pages.

Saeki et al., "Upper and lower critical solution temperatures in poly (ethylene glycol) solutions" Polymer, vol. 17, No. 8, Aug. 1976, 685-689, 5 pages.

Sammes and Yshioglu, "Modern bioassays using metal chelates as luminescent probes" Natural Product Reports, vol. 31, No. 1, 1996, 28 pages.

Sanni et al., "A field case study of inter-well chemical tracer test" in SPE International Symposium on Oilfield Chemistry, Society of Petroleum Engineers, Apr. 2015, 17 pages.

Sanni et al., "Pushing the envelope of residual oil measurement: A field case study of a new class of inter-well chemical tracers" Journal of Petroleum Science and Engineering, vol. 163, 2018, 19 pages.

Santarelli et al., "Formation Evaluation From Logging on Cuttings" SPE Reservoir Evaluation and Engineering, presented at the 1996 SPE Permian Basin Oil and Gas Recovery Conference, Mar. 27-29, 1996, published Jun. 1998, 7 pages.

Schmidt et al., "Copper dipicolinates as peptidomimetic ligands for the Src SH2 domain" Bioorganic & Medicinal Chemistry Letters, 14(16), 4203-4206, Aug. 2004, 4 pages.

Schmidt et al., "Synthesis of Mono- and Dinuclear Vanadium Complexes and Their Reactivity toward Dehydroperoxidation of Alkyl Hydroperoxides" Inorganic Chemistry 56(3), 2017, 1319-1332, 14 pages.

Selvin et al., "Principles and biophysical applications of lanthanide-based probes" Annual Review of Biophysics and Biomolecular Structure, Jun. 2002, 28 pages.

Serres-Piole et al., "Direct sensitive simultaneous determination of fluorinated benzoic acids in oil reservoir waters by ultra high-performance liquid chromatography-tandem mass spectrometry" Journal of Chromatography A, 1218, Aug. 2011, 6 pages.

Serres-Piole et al., "Water tracers in oilfield applications: Guidelines" Elsevier Ltd., Journal of Science and Engineering, Nov. 2012, 18 pages.

ShamsiJazeyi et al., "Polymer-Coated Nanoparticles for Enhance Oil Recovery" Journal of Applied Polymer Science, vol. 131, No. 15, Aug. 5, 2014, 13 pages.

Shook et al., "SPE 124614: Determining Reservoir Properties and Flood Performance from Tracer Test Analysis" Society of petroleum Engineers (SPE), presented at SPE Annual Technical Conference and Exhibition, Oct. 4-7, 2009, 19 pages.

Silva et al., "Studies on new chemical tracers for determination of residual oil saturation in the inter-well region." SPE Oklahoma City Oil and Gas Symposium. OnePetro, Mar. 2017, 14 pages.

Solomon et al., "Synthesis and Study of Silver Nanoparticles" Journal of Chemical Education vol. 84, No. 2, 2007, 332-325, 4 pages.

Song et al., "SERS-Encoded Nanogapped Plasmonic Nanoparticles: Growth of Metallic Nanoshell by Templating Redox-Active Polymer Brushes" Journal of the American Chemical Society (JACS), Apr. 28, 2014, 4 pages.

Stiles et al., "Surface-Enhanced Raman Spectroscopy" Annual Review of Analytical Chemistry, vol. 1, No. 1, Jul. 2008, 601-626, 29 pages.

Stryer et al., "Diffusion-enhanced fluorescence energy transfer" Annual Review of Biophysics and bioengineering, vol. 11, Issue 1, 1982, 21 pages.

Su et al., "A Dipicolinic Acid Tag for Rigid Lanthanide Tagging of Proteins and Paramagnetic NMR Spectroscopy" Journal of the American Chemical Society, 130(32), Jul. 2008, 10486-10487, 2 pages.

Sýkora et al., "Recent advances in mixed-mode chromatographic stationary phases." Journal of separation science 42.1, Jan. 2019, 89-129, 75 pages.

Takenaka et al., "Effect of fatty acids on the membrane fluidity of cultured chick dorsal root ganglion measured by fluorescence photobleaching recovery." Journal of neurobiology 14.6, Nov. 1983, 457-461, 5 pages.

Tang et al., "Synthesis and fluorescence properties of Tb(III) complexes with pyridine-2,6-dicarboxylic acid derivatives" Journal of Central South University of Technology (English Edition), 15(5), Oct. 2008, 599-605, 7 pages.

Tang et al., "Synthesis of Novel Derivatives of Pyridine-2,6-dicarboxylic Acid" Synthetic Communications: An International Journal for Rapid Communication of Synthetic Organic Chemistry, 36(14), Jun. 2006, 2027-2034, 9 pages.

Tang et al., "Synthesis of Eu(III) and Tb(III) Complexes with Novel Pyridine-2,6-Dicarboxylic Acid Derivatives and Their Fluorescence Properties" Front. Chem. China, 2006, 4:, 408-413, 6 pages.

(56) References Cited

OTHER PUBLICATIONS

Thomas et al., "Deployment and Detection of a Novel Barcoded Advanced Tracers System for the Optimization of Improved Waterflood Recovery in Hydrocarbon Reservoirs" SPE-194872-MS, SPE Middle East Oil and Gas Show and Conference. Society of Petroleum Engineers, 2019, 10 pages.

Tian et al., "Off-Resonant Gold Superstructures as Ultrabright Minimally Invasive Surface-Enhanced Raman Scattering (SERS) Probes" American Chemical Society, Jul. 2015, 7 pages.

Toulhoat, "Experimentation and Modelling of U, Th and Lanthanides Transport in Fissured Rocks: Influence of Complexation" MRS Proceedings, vol. 50, Jan. 1, 1985, 8 pages.

Wahajuddin et al., "Superparamagnetic iron oxide nanoparticles: Magnetic nanoplatforms as drug carriers" International Journal of Nanomedicine, 7, Jul. 2012, 3445-3471, 27 pages.

Wang et al., "The Design and Implementation of a Full Field Inter-Well Tracer Program on a Giant UAE Carbonate Oil Field" in Abu Dhabi International Petroleum Exhibition and Conference, Society of Petroleum Engineers, SPE-177527-MS, Nov. 2015, 8 pages.

Wu et al., "A reusable biosensor chip for SERS-fluorescence dual mode immunoassay" Proc. SPIE 9543, Third International Symposium on Laser Interaction with Matter, 954317, May 4, 2015, 6 pages.

Wu et al., "A SERS-Assisted 3D Barcode Chip for High-Throughput Biosensing" Small Journal vol. 11, No. 23, Jun. 11, 2015, 9 pages.

Xu et al., "Superparamagnetic Photonic Crystals" Adv. Mater., Nov. 2001, 13, 1681-1683, 4 pages.

Xu et al., "Synthesis and Utilization of Monodisperse Superparamagnetic Colloidal Particles for Magnetically Controllable Photonic Crystals" Chem. Mater., 14(3), 2002, 1249-1256, 8 pages.

Xu et al.., "Measurement of two-photon excitation cross sections of molecular fluorophores with data from 690 to 1050 nm" Journal of the Optical Society of America B, Mar. 1996, 11 pages.

Yang et al., "The Co-Luminescence Groups of Sm-La-pyridyl Carboxylic Acids and the Binding Characteristics between the Selected Doped Complex and Bovine Serum Albumin" Bulletin of the Korean Chemical Society 33(4), Apr. 20, 2012, 1303-1309, 7 pages.

Yang et al., "Paramagnetic labeling of proteins and pseudocontact shift in structural biology" Chinese Journal of Magnetic Resonance, 2014, 31(2): 155-171, 12 pages (English Abstract).

Yu et al., "Adsorption of proteins and nucleic acids on clay minerals and their interactions: A review" Applied Clay Science, 80-81, Aug. 2013, 443-452, 10 pages.

Zamberi et al., "SPE 166005: Improved Reservoir Surveillance Through Injected Tracers In A Saudi Arabian Field: Case Study" Society of Petroleum Engineers (SPE), presented at SPE Reservoir Characterization and Simulation Conference and Exhibition, Sep. 2013, 15 pages.

Zemel, "Chapter 3: Interwell Water Tracers" Tracers in the Oil Field, vol. 43, 1st Edition, Elsevier Science, Jan. 13, 1995, 47 pages.

Zhang et al., "Water adsorption on kaolinite and illite after polyamine adsorption" Journal of Petroleum Science and Engineering, 142, Jun. 2016, 13-20, 8 pages.

Zhao et al., "Chromatographic Separation of Highly Soluble Diamond Nanoparticles Prepared by Polyglycerol Grafting" Angewandte Chemie International Edition, vol. 50, No. 6, Feb. 7, 2011, 1388-1392, 5 pages.

Zheng et al., "Immobilization of Candida rugosa lipase on hydrophobic/ strong cation-exchange functional silica particles for biocatalytic synthesis of phytosterol esters." Bioresource technology 115, Jul. 2012, 141-146, 6 pages.

Zhou et al., "Upconversion luminescent materials: advances and applications" Chem Rev., Jan. 14, 2015, 71 pages.

Liu et al., "Self-Aggregating Deep Cavitand Acts as a Fluorescence Displacement Sensor for Lysine Methylation," J. Am. Chem. Soc., 2016, 138:10746-10749, 4 pages.

Ghanem et al., "Investigation of Fluorescent Dyes as Partitioning Tracers for Subsurface Nonaqueous Phase Liquid (NAPL) Characterization," Journal of Environmental Engineering, Aug. 2003, 5 pages.

U.S. Appl. No. 17/835,676, Wang, Fluorescent Dye Oil Tracer Compositions, filed Jun. 8, 2022, 76 pages.

Busschaert et al., "Towards Predictable Transmembrane Transport: QSAR Analysis of Anion Binding and Transport," Chemical Science, May 2013, 4:3036-3045, 11 pages.

Dyson et al., "The Synthesis of Alkylthiocarbimides and their Thiocarbamide Derivatives by Means of Thiocarbonyl Chloride," Recueil des Travaux Chimiques des Pays-Bas, 1926, 45:421-423, 4 pages.

Kumavat et al., "Green Synthesis of Symmetrical N, N'-disubstituted Thiourea Derivatives in Water Using Solar Energy," Environmental Chemistry Letters, Jan. 2013, 11:177-182, 6 pages.

Lindahl et al., "Determination of Volatile Amines in Air by Diffusive Sampling, Thiourea Formation and High-Performance Liquid Chromatography," Journal of Chromatography, Jul. 1993, 643(1-1):35-41, 7 pages.

Techapanalai, "Tetrabromomethane-mediated Desulfurization for Synthesis of Isothiocyanates from Amines," Thesis for the degree of Master of Science in Chemistry, Chulalongkorn University, 2020, 160 pages.

* cited by examiner

FLUORESCENT DYE MOLECULES HAVING HYDROPHILICITY AND HYDROPHOBICITY FOR TRACER APPLICATIONS

TECHNICAL FIELD

This document relates to methods and compositions used in generating and using functionalized fluorescent tracers in drilling and oil well applications.

BACKGROUND

Tracer techniques can be a powerful diagnostic tool in numerous scientific disciplines and for technologies in many industrial sectors. Molecular tracers can include water-soluble or oil-soluble compounds. In field tests of oilfields, water-soluble tracers can provide a better understanding of the studied oil reservoir, for example, a better understanding of inter-well connections, connections between layers and heterogeneities. Similarly, oil-soluble tracers can provide information on petroleum products, for example qualitative analysis of the production fluid return from multiple stage completions, either vertical or horizontal completions.

SUMMARY

This disclosure describes functionalized fluorescent tracers, methods of making the tracers, and methods of using the tracers.

In some implementations, a composition includes a functionalized fluorescent dye. The functionalized fluorescent dye includes an isothiocyanate-containing dye functionalized with a functional group that includes a primary amine. The isothiocyanate-containing dye is selected from the group consisting of fluorescein isothiocyanate, Rhodamine B isothiocyanate, or tetramethylrhodamine isothiocyanate, or any isoform thereof. The functional group comprises a primary amine is selected from Group I, Group II, or Group III. Group I consists of ethylamine, propylamine, isopropylamine, butylamine, tert-butylamine, hexylamine, octylamine, decylamine, dodecylamine, tetradecylamine, and hexadecylamine. Group II consists of aniline, benzylamine, phenethylamine, 3-phenyl propylamine, 4-phenylbutylamine, and 6-phenylhexan-1-amine. Group III consists of 4-fluoroaniline, 3,4-difluoroaniline, 2,4,6-trifluoroaniline, 4-(trifluoromethyl)aniline, 3,5-bis(trifluoromethyl)aniline, 2,4,6-tris(trifluoromethyl)aniline, 4-fluoro-3-(trifluoromethyl)aniline, 4-(trifluoromethoxy)aniline, 4-fluorobenzylamine, 2,4-difluorobenzylamine, 2,3,4-trifluorobenzylamine, 3-(trifluoromethyl)benzylamine, and 3,5-bis(trifluoromethyl)benzylamine.

In some implementations, method of making a functionalized fluorescent dye, includes dissolving a water-soluble isothiocyanate-containing fluorescent dye in an aqueous solvent to yield an aqueous dye solution. The water-soluble isothiocyanate-containing fluorescent dye is selected from the group consisting of fluorescein isothiocyanate, Rhodamine B isothiocyanate, or tetramethylrhodamine isothiocyanate, or any isoform thereof. The method includes dissolving a functional group including a primary amine in an organic solvent to yield an organic functional group solution. The functional group that includes a primary amine is selected from Group I, Group II, or Group III. Group I consists of ethylamine, propylamine, isopropylamine, butylamine, tert-butylamine, hexylamine, octylamine, decylamine, dodecylamine, tetradecylamine, and hexadecylamine. Group II consists of aniline, benzylamine, phenethylamine, 3-phenyl-1-propylamine, 4-phenylbutylamine, and 6-phenylhexan-1-amine. Group III consists of 4-fluoroaniline, 3,4-difluoroaniline, 2,4,6-trifluoroaniline, 4-(trifluoromethyl)aniline, 3,5-bis(trifluoromethyl)aniline, 2,4,6-tris(trifluoromethyl)aniline, 4-fluoro-3-(trifluoromethyl)aniline, 4-(trifluoromethoxy)aniline, 4-fluorobenzylamine, 2,4-difluorobenzylamine, 2,3,4-trifluorobenzylamine, 3-(trifluoromethyl)benzylamine, and 3,5-bis(trifluoromethyl)benzylamine. The method includes forming an emulsion of the aqueous dye solution and the organic functional group solution, and extracting the functionalized fluorescent dye from the organic functional group solution, wherein the functionalized fluorescent dye is a reaction product of the water-soluble isothiocyanate-containing dye and the functional group that includes a primary amine.

In some implementations, a method of tracing fluid flow in a subterranean formation includes mixing a functionalized fluorescent tracer into a fluid to yield a tracer fluid. The functionalized fluorescent tracer includes an isothiocyanate-containing fluorescent dye functionalized with a functional group that includes a primary amine. The isothiocyanate-containing fluorescent dye is selected from the group consisting of fluorescein isothiocyanate, Rhodamine B isothiocyanate, or tetramethylrhodamine isothiocyanate, or any isoform thereof. The functional group that includes a primary amine is selected from Group I, Group II, or Group III. Group I consists of ethylamine, propylamine, isopropylamine, butylamine, tert-butylamine, hexylamine, octylamine, decylamine, dodecylamine, tetradecylamine, hexadecylamine, and octadecylamine. Group II consists of aniline, benzylamine, phenethylamine, 3-phenyl-1-propylamine, 4-phenylbutlamine, and 6-phenylhexan-1-amine. Group III consists of 4-fluoroaniline, 3,4-difluoroaniline, 2,4,6-trifluoroaniline, 4-(trifluoromethyl)aniline, 3,5-bis(trifluoromethyl)aniline, 2,4,6-tris(trifluoromethyl)aniline, 4-fluoro-3-(trifluoromethyl)aniline, 4-(trifluoromethoxy)aniline, 4-fluorobenzylamine, 2,4-difluorobenzylamine, 2,3,4-trifluorobenzylamine, 3-(trifluoromethyl)benzylamine, and 3,5-bis(trifluoromethyl)benzylamine. The method includes flowing the tracer fluid into a first subterranean formation, recovering a sample from the first subterranean formation or a second subterranean formation, analyzing the sample for a fluorescent signal, and further separating the sample and analyzing the sample for a barcode functional group.

The details of one or more implementations of the disclosure are set forth in the accompanying drawings and the description that follows. Other features, objects, and advantages of the disclosure will be apparent from the description and drawings, and from the claims.

DETAILED DESCRIPTION

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Figure 1:
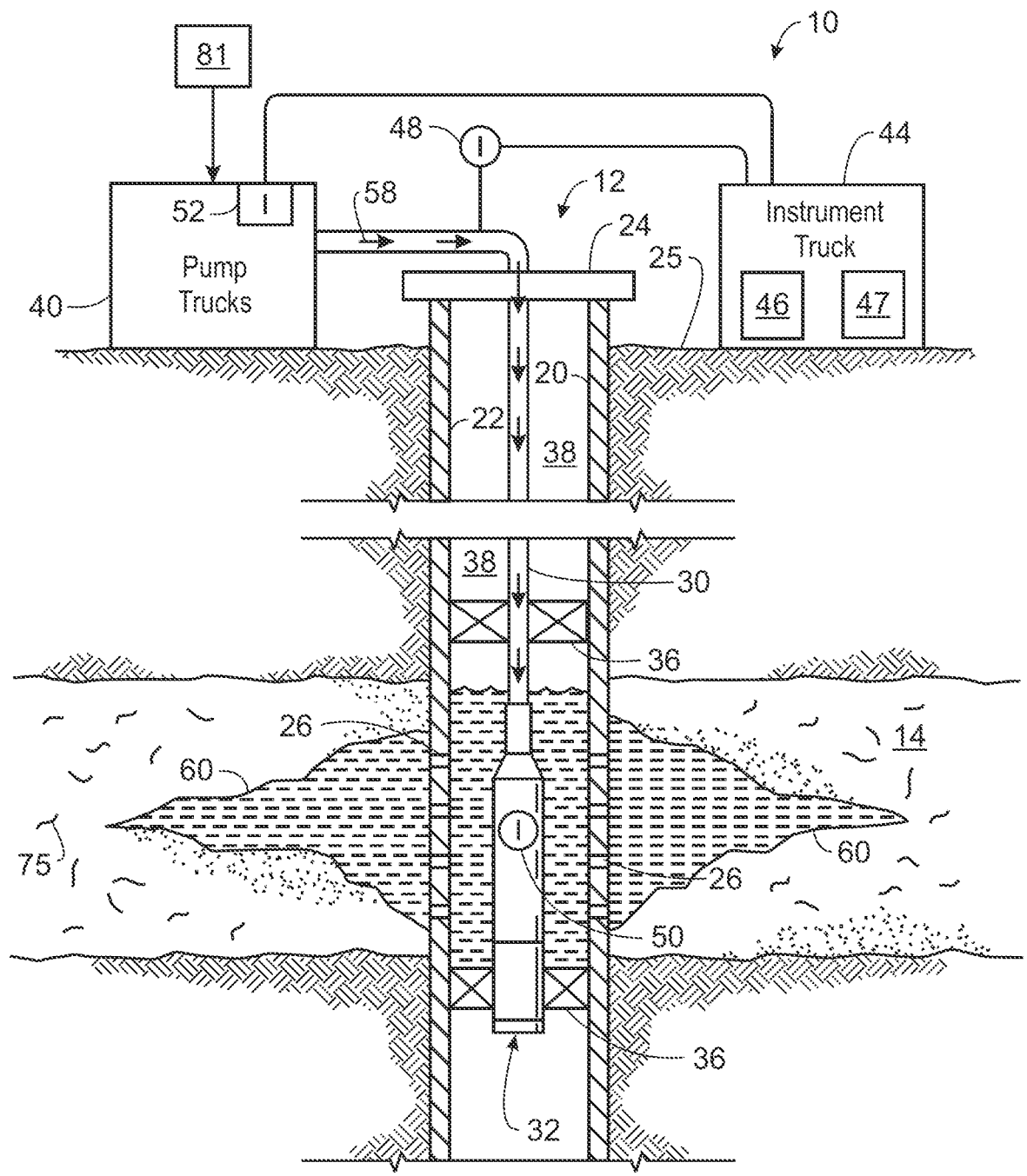
FIG. 1 shows an example of a fracture treatment for a well.

FIG. 1 illustrates an example of a drilling operation 10 for a well 12. The well 12 can be in a wellbore 20 formed in a subterranean zone 14 of a geological formation in the Earth's crust. The subterranean zone 14 can include, for example, a formation, a portion of a formation, or multiple formations in a hydrocarbon-bearing reservoir from which recovery operations can be practiced to recover trapped hydrocarbons. Examples of unconventional reservoirs include tight-gas sands, gas and oil shales, coalbed methane, heavy oil and tar sands, gas-hydrate deposits, to name a few. In some implementations, the subterranean zone 14 includes an underground formation including natural fractures 60 in rock formations containing hydrocarbons (for example, oil, gas, or both). For example, the subterranean zone 14 can include a fractured shale. In some implementations, the well 12 can intersect other suitable types of formations, including reservoirs that are not naturally fractured in any significant amount.

The well 12 can include a casing 22 and well head 24. The wellbore 20 can be a vertical, horizontal, deviated, or multilateral bore. The casing 22 can be cemented or otherwise suitably secured in the wellbore 20. Perforations 26 can be formed in the casing 22 at the level of the subterranean zone 14 to allow oil, gas, and by-products to flow into the well 12 and be produced to the surface 25. Perforations 26 can be formed using shape charges, a perforating gun, or otherwise.

For a drilling treatment 10, a work string 30 can be disposed in the wellbore 20. The work string 30 can be coiled tubing, sectioned pipe, or other suitable tubing. A drilling tool or drill bit 32 can be coupled to an end of the work string 30. Packers 36 can seal an annulus 38 of the wellbore 20 uphole of and downhole of the subterranean zone 14. Packers 36 can be mechanical, fluid inflatable, or other suitable packers.

One or more pump trucks 40 can be coupled to the work string 30 at the surface 25. The pump trucks 40 pump drilling mud 58 down the work string 30 to lubricate and cool the drilling tool or drill bit 32, maintain hydrostatic pressure in the wellbore, and carry subterranean cuttings to the surface. The drilling mud 58 can include a fluid pad, proppants, flush fluid, or a combination of these components. The pump trucks 40 can include mobile vehicles, equipment such as skids, or other suitable structures.

One or more instrument trucks 44 can also be provided at the surface 25. The instrument truck 44 can include a drilling control system 46 and a drilling simulator 47. The drilling control system 46 monitors and controls the drilling treatment 10. The drilling control system 46 can control the pump trucks 40 and fluid valves to stop and start the drilling treatment 10. The drilling control system 46 communicates with surface and subsurface instruments to monitor and control the drilling treatment 10. In some implementations, the surface and subsurface instruments may comprise surface sensors 48, down-hole sensors 50, and pump controls 52.

Additives 81 can be mixed with drilling mud 58 or other drilling fluids and flowed through the reservoir. In some implementations, the additives 81 can include one or more tracers, for example, a fluorescent dye. Hydrophilic fluorescent dyes can be used as water-soluble tracers. These conventional dyes are inexpensive and easy to use. Examples of fluorescent dyes include fluorescein, eosin, Rhodamine, and Rhodamine-B. However, duo to their poor hydrophobicity, these hydrophilic dye tracers cannot be used as partition tracers which partition between the aqueous and the oil phase. In addition, the number of tracers is limited to the number of organic dye molecules available.

The tracers described herein overcome these shortcomings. These tracers can be generated using a synthetic method to tune the hydrophilicity/hydrophobicity of water-soluble dye molecules by chemically modifying the molecular structure of the molecule. For example, by covalently grafting functional groups onto the dye molecules, the various functional groups can create barcoded structural information, resulting in new compounds. In some embodiments, by introducing hydrophobic functional groups into water-soluble dye molecules, the hydrophobicity of the resulting molecules can be enhanced, thus improving their solubility in an oil phase. By tailoring the molecules, the hydrophilicity and hydrophobicity of the molecule can be adjusted to a desired degree. Therefore, the partition of the molecule in an oil phase is controllable. This, in part, enables the potential application of these functionalized fluorescent dyes as partition tracers for oil reservoir applications. The structure-modified dyes reserve their fluorescence properties, although in some implementations the fluorescence features may also be modified by the introduction of functional groups. In some implementations, a fluorinated hydrophobic functional group can be introduced, resulting in dye compounds with low sorption on rock in fluids.

These functionalized fluorescent dyes are described herein as barcoded or having barcode information. In this context, "barcode" refers to the fact that these functionalized dyes or tracers are uniquely identifiable two or more orthogonal analyses. As a first factor, the tracers can be identified by their fluorescence signal, for example, by the wavelength of the emission spectrum or simply by the presence of a fluorescent signal. As a second factor, the tracers can be identified by their mass or hydrophobicity. Accordingly, the unique combinations of the different fluorophores and the different functionalization groups results in a library of barcoded tracers.

Barcoded tracers have several advantages. For example, different combinations of different tracers can be used simultaneously or in parallel to provide information about drilling operations or subterranean formations. For example, two or more uniquely identifiable tracers can be injected at two or more different drilling sites and can yield information about inter well connectivity. In another example, uniquely identifiable tracers can be injected at the same drilling site at different times, can yield temporal information about transit time, depth, or length of subterranean fractures or formations.

Further, the two-factor nature of the barcode tracers allows for an advantageous two-factor analysis. The first factor, the fluorescence signal, can be detected in an initial, rapid analysis. Accordingly, samples recovered from a drilling operation or subterranean formation can be quickly and qualitative analyzed for the presence of a fluorescence signal, i.e., a 'yes/no' analysis. In some implementations, this first analysis can be done on-site, and samples exhibiting a fluorescence signal can be allocated for further processing. Next, the samples exhibiting a fluorescence signal can be subsequently analyzed for mass or hydrophobicity, for example by high performance liquid chromatography (HPLC), mass spectrometry, liquid chromatography-mass spectrometry (LC-MS), or pyrolysis gas chromatography-mass spectrometry (Pyrolysis-GC-MS) analysis.

A chemical method to modify the structures of conventional dye molecules by introducing molecular barcode information and by tailoring the hydrophilicity and/or hydrophobicity of the conventional water-soluble dye molecules is described herein. The resulting compounds expand the number of dyes available for tracer applications as water-soluble tracers, oil tracers, or partition tracers.

The new dye molecules include the general structure $R_I$—X—$R_{II}$, where $R_I$ is a fluorescent fluorophore. The fluorophore can be either hydrophilic or hydrophobic, and can be detectable by optical methods, for example, florescence imaging or molecular spectroscopy (absorbance or fluorescence). In the general structure, X can be a linking molecule. X can be selected from the group that includes $C_{1-18}$ alkylene, $C_{1-18}$ alkenylene, or $C_{1-18}$ alkynylene, where each of $C_{1-18}$ alkylene, $C_{1-18}$ alkenylene, $C_{1-18}$ alkynylene can be optionally replaced or interrupted by any one of oxygen (O), sulfur (S), or an amine (NH). In the general structure, Ru can be selected from the group that includes hydrogen, alkoxy, haloalkoxy (including Cl, Br, or I), aryl, or heteroaryl (with N, NH, O, and S). The Ru confers a molecular fingerprint or barcode structure into the new compounds. The new $R_I$—X—$R_{II}$ compounds are detectable by spectroscopy methods, for example, UV-Visible spectroscopy (UV-Vis), fluorescence, Fourier-transform infrared spectroscopy (MIR), Raman spectroscopy, mass spectroscopy, or chromatography (HPLC or LC-MS).

In some implementations, the fluorescent dye Ru is fluorescein isothiocyanate (FITC), Rhodamine B isothiocyanate (RBITC), or tetramethylrhodamine isothiocyanate (MRITC/TRITC), or any isomer thereof. The structures of FITC, RBITC, and MRITC/TRITC are shown in Table 1. These dyes are highly water-soluble, i.e., hydrophilic, and have fluorescence emissions in the visible spectral region. The excitation and emission wavelengths of these dyes are listed in Table 1.

TABLE 1

Water-Soluble Dyes and their Molecular Structure

| Dye compound | Molecular structure; Molecular weight | Fluorescence $\lambda_{excitation}$/ $\lambda_{emission}$ | CAS Number/ Isomers |
| --- | --- | --- | --- |
| Fluorescein isothiocyanate (FITC) | 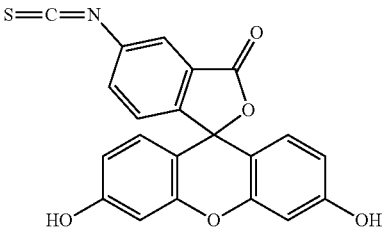<br>MW = 389.38 | 495 nm/519nm | 27072-45-3 (mixed isomers)<br>3326-32-7 (5-isomer)<br>18861-78-4 (6-isomer) |
| Rhodamine B isothiocyanate (RBITC) | 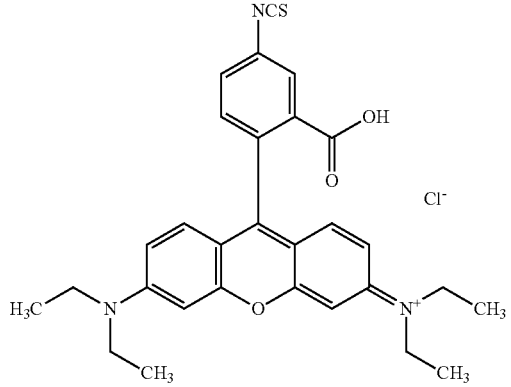<br>MW = 536.08 | 570 nm/ 595 nm | 36877-69-7 (mixed isomers) |

TABLE 1-continued

Water-Soluble Dyes and their Molecular Structure

| Dye compound | Molecular structure; Molecular weight | Fluorescence $\lambda_{excitation}/\lambda_{emission}$ | CAS Number/ Isomers |
|---|---|---|---|
| Tetramethylrhodamine isothiocyanate (MRITC/TRITC) | 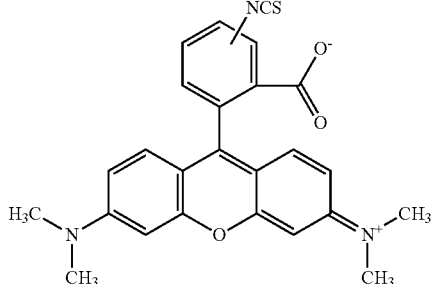<br>MW = 443.52 | 544 nm/ 570 nm | 95197-95-8 (mixed isomers) 80724-20-5 (Isomer R) 80724-19-2 (5-TRITC) |

The dyes shown in Table 1 were each modified with additional functional groups. The functional groups are added using the reaction of a primary amine with an isothiocyanate to result in a substituted thiourea, as shown in Equation 1.

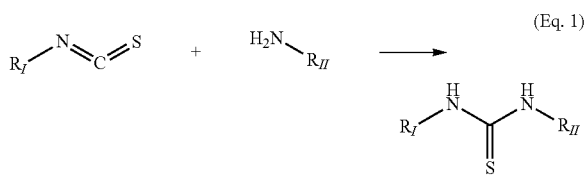 (Eq. 1)

$R_{II}$ is an alkyl, aromatic, heterocyclic group, or other suitable amine-containing functional group, and $R_I$ is the isothiocyanate-containing fluorescent dye, where in Equation 1 the isothiocyanate group is expanded for clarity.

Figure 2:
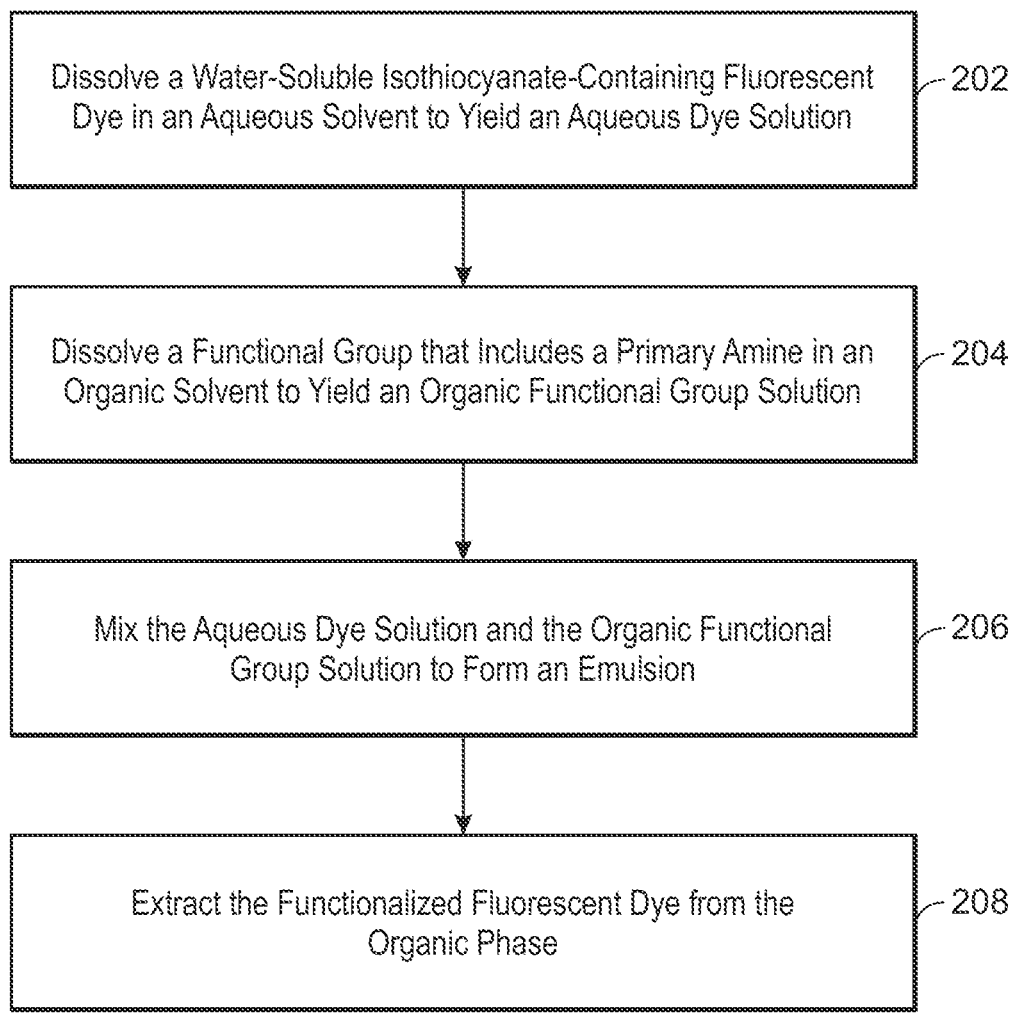
FIG. 2 is a flow chart of an example method of making a functionalized fluorescent dye.

FIG. 2 is a flow chart of an example method 200 of making a functionalized fluorescent dye. The reactions were performed at room temperature in a bi-phase system. At 202, a water-soluble isothiocyanate-containing fluorescent dye is dissolved in an aqueous solvent to yield an aqueous dye solution. For example, a water-soluble isothiocyanate-containing dye can be dissolved in deionized water. At 204, a functional group that includes a primary amine is dissolved in an organic solvent to yield an organic functional group solution. For example, an amino compound can be dissolved in chloroform. The two solutions each contain the same molecular molar concentration of amino compound and dye. At 206, the aqueous dye solution and the organic functional group solution are mixed to form an emulsion. The two solutions are mixed in equal volume and stirred vigorously until the two-phase solutions formed an emulsion. The reaction is allowed to continue under stirring for at least 12 hours. Upon completion of the reaction, the stirring was stopped and the emulsion was allowed to settle into two phases. At 208, the functionalized fluorescent dye is extracted from the organic phase. It can be observed by color that the dye is transferred from the aqueous phase to the organic phase. In some implementations, the organic solvent is evaporated by $N_2$ bubbling or heating. The obtained solid powder samples can be redispersed into different organic solvents.

Tables 2-4 illustrate different amine-containing functional groups that can be used to functionalize an isothiocyanate dye. The amine-containing functional groups shown in Tables 2-4 can also be referred to as barcode functional groups. The compounds shown in Table 2 are primary amine compounds with alkyl groups. The hydrocarbon chains have different lengths and provide both barcode information and the ability to tailor the hydrophobicity of the resulting compound, based on, for example, alkyl chain length. Accordingly, isothiocyanate dyes functionalized with the compounds listed in Table 2 have variable partitioning in oil phases.

The compounds in Table 3 are phenyl-based compounds with hydrocarbon chains of different lengths in their structures. Compared to the compounds with alkyl chains in Table 2, the phenyl based aromatic structures with hydrocarbon chains are more hydrophobic and can have increased miscibility with oils, which provides both barcode information and the ability to tailor the hydrophobicity of the resulting compound, based on, for example, alkyl chain length. The compounds resulting from the reaction of an isothiocyanate dye and the phenyl based aromatic structures in Table 3 have variable partitioning in oil phases.

The compounds in Table 4 are fluorinated benzene based aromatic compounds. Fluorinated compounds usually have very low sorption on rocks. Compared to the compounds in Table 2 and 3, the fluorinated benzene based aromatic compounds are more hydrophobic and can have increased miscibility with oils. By introducing the fluorinated aromatic functional groups into dye molecules, the resulting functionalized dyes have variable hydrophobicity and barcode information. The functionalized dye including a fluorinated benzene based aromatic functional group have low retention in rocks and subterranean formations, and therefore can be used as partition tracers with variable hydrophobicity.

TABLE 2

Primary Amine Compounds with Alkyl Groups

| Compound | Molecular Structure/Weight (Da) | | CAS number |
|---|---|---|---|
| Ethylamine | $CH_3—CH_2—NH_2$ | 45.08 | 75-04-7 |
| Propylamine | $CH_3—(CH_2)_2—NH_2$ | 59.11 | 107-10-8 |
| Isopropylamine | $(CH_3)_2—CH—NH_2$ | 59.11 | 75-31-0 |

TABLE 2-continued

Primary Amine Compounds with Alkyl Groups

| Compound | Molecular Structure/Weight (Da) | | CAS number |
|---|---|---|---|
| Butylamine | $CH_3-(CH_2)_3-NH_2$ | 73.14 | 109-73-9 |
| tert-Butylamine | $(CH_3)_3-C-NH_2$ | 73.14 | 75-64-9 |
| Hexylamine | $CH_3-(CH_2)_5-NH_2$ | 101.19 | 111-26-2 |
| Octylamine | $CH_3-(CH_2)_7-NH_2$ | 129.24 | 111-86-4 |
| Decylamine | $CH_3-(CH_2)_9-NH_2$ | 157.30 | 2016-57-1 |
| Dodecylamine | $CH_3-(CH_2)_{11}-NH_2$ | 185.35 | 124-22-1 |
| Tetradecylamine | $CH_3-(CH_2)_{13}-NH_2$ | 213.40 | 2016-42-4 |
| Hexadecylamine | $CH_3-(CH_2)_{15}-NH_2$ | 241.46 | 143-27-1 |
| Octadecylamine | $CH_3-(CH_2)_{17}-NH_2$ | 269.51 | 124-30-1 |

TABLE 3

Phenyl Based Aromatic Compounds with Primary Amino Groups

| Compound | Molecular Structure/Weight (Da) | CAS number |
|---|---|---|
| Aniline | 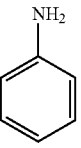 93.13 | 62-53-3 |
| Benzylamine | 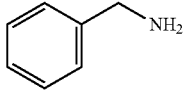 107.15 | 100-46-9 |
| Phenethylamine | 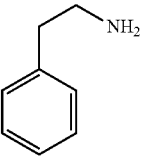 121.18 | 64-04-0 |
| 3-Phenyl-1-propylamine | 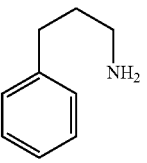 135.21 | 2038-57-5 |
| 4-Phenylbutylamine | 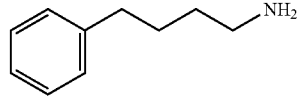 149.24 | 13214-66-9 |

TABLE 3-continued

Phenyl Based Aromatic Compounds with Primary Amino Groups

| Compound | Molecular Structure/Weight (Da) | CAS number |
|---|---|---|
| 6-phenylhexan-1-amine | 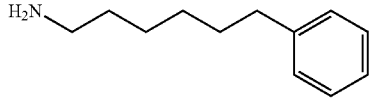 177.291 | 17734-20-2 |

TABLE 4

Fluorinated Benzene Based Aromatic Compounds with Primary Amino Group

| Compound | Molecular Structure/Weight (Da) | CAS number (Isomers) |
|---|---|---|
| 4-Fluoroaniline | 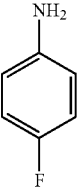 111.12 | 371-40-4<br>348-54-9<br>372-19-0 |
| 3,4-Difluoroaniline | 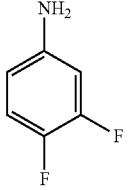 129.11 | 3863-11-4<br>4519-40-8<br>372-39-4<br>367-30-6<br>367-25-9<br>5509-65-9 |
| 2,4,6-Trifluoroaniline | 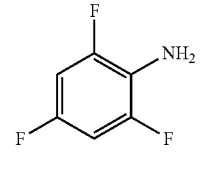 147.10 | 363-81-5<br>163733-96-8<br>3862-73-5 |
| 4-(Trifluoromethyl)aniline | 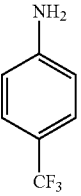 161.12 | 455-14-1<br>98-16-8<br>88-17-5 |

TABLE 4-continued

Fluorinated Benzene Based Aromatic Compounds with Primary Amino Group

| Compound | Molecular Structure/ Weight (Da) | CAS number (Isomers) |
|---|---|---|
| 3,5-Bis(trifluoromethyl)aniline | 229.12 | 328-74-5 328-93-8 |
| 2,4,6-Tris(trifluoromethyl)aniline | 297.12 | 25753-22-4 |
| 4-Fluoro-3-(trifluoromethyl)aniline | 179.11 | 2357-47-3 |
| 4-(Trifluoromethoxy)aniline | 177.12 | 461-82-5 1535-73-5 1535-75-7 |
| 4-Fluorobenzylamine | 125.14 | 140-75-0 100-82-3 89-99-6 |
| 2,4-Difluorobenzylamine | 143.13 | 72235-52-0 72235-53-1 69385-30-4 72235-51-9 |
| 2,3,4-Trifluorobenzylamine | 161.12 | 235088-67-2 235088-69-4 |
| 3-(Trifluoromethyl)-benzylamine | 175.15 | 3300-51-4 2740-83-2 |
| 3,5-Bis(trifluoromethyl)-benzylamine | 243.15 | 85068-29-7 |

The dyes described herein can be used as partition tracers in subterranean applications. For example, multistage hydraulic fracturing along a horizontal well is key to effectively recover hydrocarbons from tight reservoirs. Improving the hydrocarbon recovery requires detailed production information of each hydraulic fracture. Water-soluble chemical tracers are often used to calculate the production profile from multistage fracturing through a tracer flow back test, whereas oil-soluble tracers are used as a direct indicator to estimate the oil production contribution in individual fractures stages, for example, diagnosis of multi-zone oil flow efficiency, confirming zonal oil flow, or qualifying flow assurance. Oil-soluble tracers can also be embedded in the porous media and absorbed on the surfaces of solid carriers, which allows the tracers to be released from their carriers when oil passes through and has negligible partitioning into the water or gas phase. Partition tracers can well control the partition of a tracer between the aqueous and the oil phase and thus monitor the water phase and oil phase simultaneously.

With the barcoded oil-soluble partition tracers described herein, qualitative analysis by fluorescence spectroscopy or imaging can be used for early screening if the tracer is in the oil flow from each stage, while detailed molecular barcode information can be revealed by HPLC, LC-MS or Pyrolysis-GC-MS analysis to identify each tracer from different locations. Further, these synthesized barcoded oil-soluble compounds can also be added to mud formulations in drilling fluids as mud tracers for mud logging applications.

Figure 3:
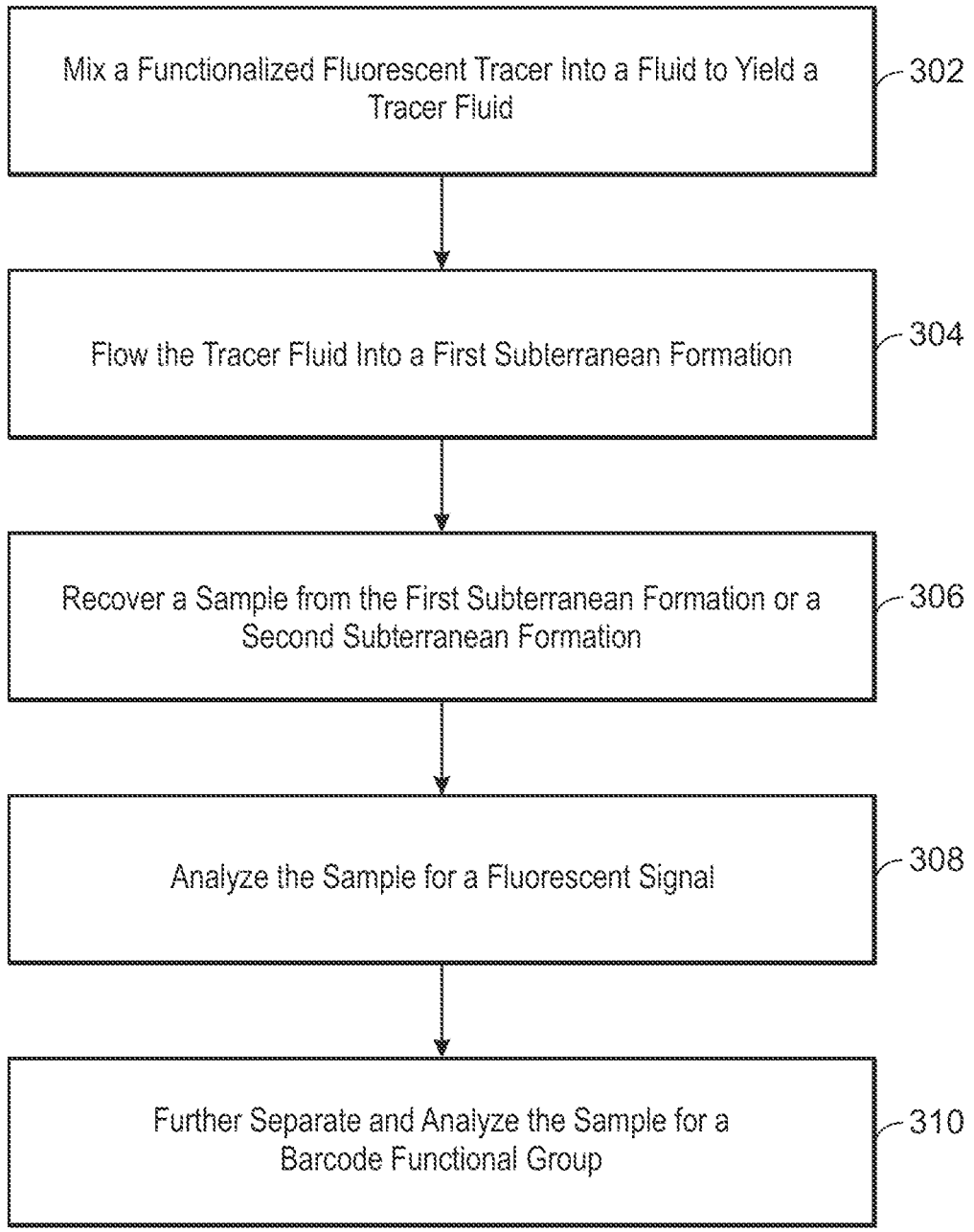
FIG. 3 is a flow chart of an example method of tracing fluid flow in a subterranean formation.

FIG. 3 is a flow chart of an example method 300 of tracing fluid flow in a subterranean formation. At 302, a functionalized fluorescent tracer is mixed into a fluid to yield a tracer fluid. At 304, the tracer fluid is flowed into a first subterranean formation. At 306, a sample is recovered from the first subterranean formation or a second subterranean formation. At 308, the sample is analyzed for a fluorescent signal. At 310, the sample is further separated and analyzed for a barcode functional group.

Figure 4:
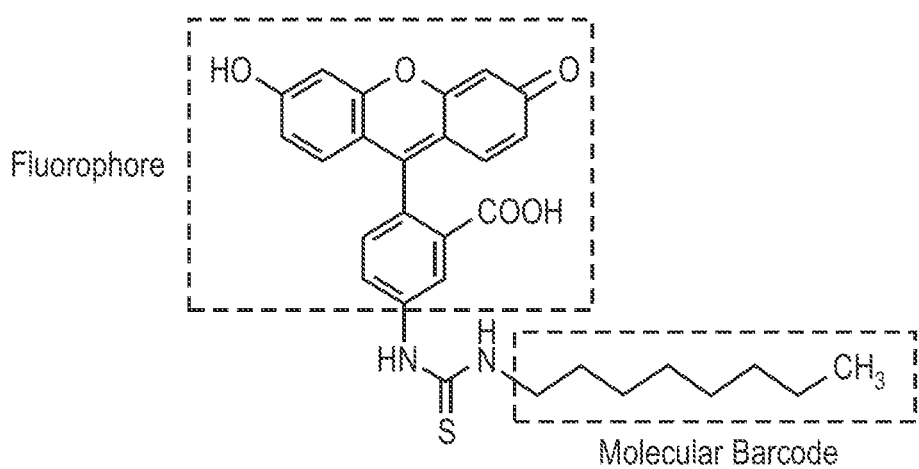
FIG. 4 shows the reaction product of fluorescein isothiocyante and 1-octylamine.

Example 1: Synthesis of FITC Functionalized With 1-octylamine 38.9 mg of FITC was dissolved in 50 mL deionized water and 12.9 mg 1-octylamine was dissolved in 50 mL benzene, respectively. Then the two solutions were mixed at 1:1 molar ration of FITC and 1-octylamine in a round bottom flask and reacted for 12 hours under vigorous stirring by a magnetic stirrer. Upon completion of the reaction, the reaction mixture was transferred into a separating funnel and left to sit overnight for phase separation. The water phase and benzene phase were collected separately. With a similar procedure, the dye FITC could be replaced by other dye molecules listed in Table 1, and the 1-octylamine can be replaced by other amines listed in Table 2. The structure of resulting isothiocyanate-amine derivative of FITC and 1-octylamine is shown in FIG. 4.

Figure 5:
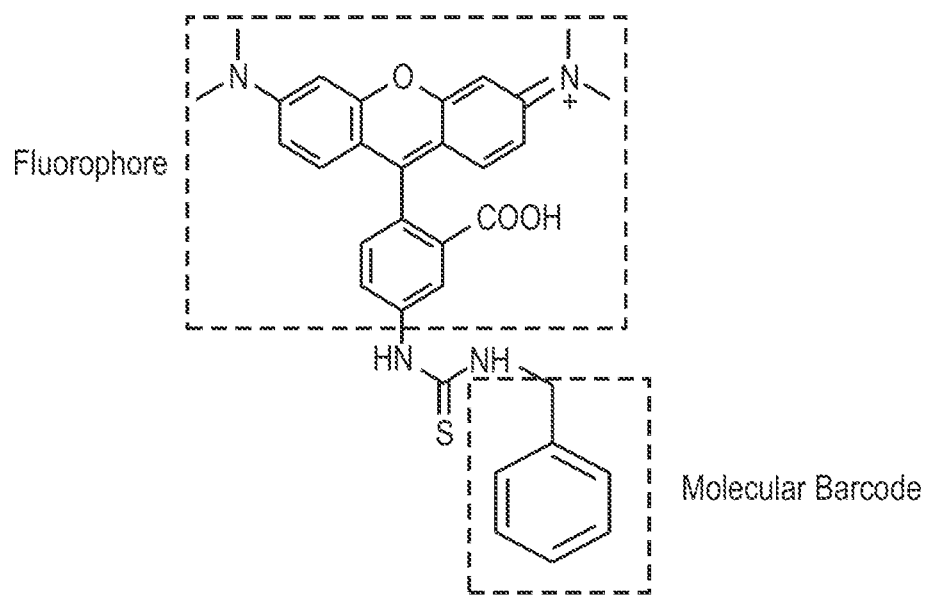
FIG. 5 shows the reaction product of Rhodamine B isothiocyanate and benzyl amine.

Example 2: Synthesis of RBITC Functionalized With Benzylamine 53.6 mg of RBITC was dissolved in 50 mL of a deionized water, and 10.7 mg benzylamine was dissolved in 50 mL chloroform, respectively. Then, the two solutions were mixed at 1:1 molar ration of RBITC and benzylamine in a round bottom flask and reacted for 12 hours under vigorous stirring by a magnetic stirrer. Upon completion of the reaction, the reaction mixture was transferred into a separating funnel and left to sit overnight for phase separation. The chloroform phase and water phase was separated and collected respectively. With a similar procedure, the dye FITC could be replaced by other dye molecules listed in Table 1 and the benzylamine could be replaced by other benzene-based amine compounds listed in Table 3. The structure of resulting isothiocyanate-amine derivative of BRITC and benzylamine is shown in FIG. 5.

Figure 6:
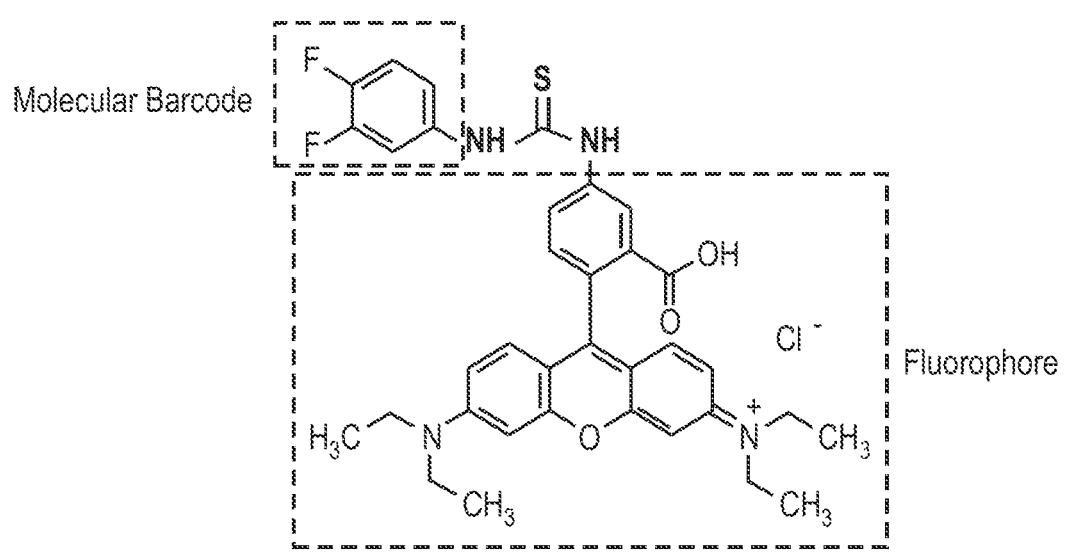
FIG. 6 shows the reaction product of tetramethylrhodamine isothiocyanate and 3,4-difluoraniline.

Example 3: Synthesis of TRITC Functionalized With 3,4,-difluoroaniline 44.4 mg of TRITC was dissolved in 50 mL of deionized water, and 12.9 mg of 3,4-difluoroaniline was dissolved in 50 mL dichloromethane, respectively. Then, the two solutions were mixed at 1:1 molar ratio of TRITC and 3,4,-difluoroaniline in a round bottom flask and reacted for 12 hours under vigorous stirring by a magnetic stirrer. Upon completion of the reaction, the reaction mixture was transferred into a separating funnel and left to sit overnight for phase separation. The dichloromethane phase and water were collected separately. With a similar procedure, the dye TRITC could be replaced by the dye molecules listed in Table 1, and the 3,4-difluoroaniline could be replaced by other fluorinated aromatic compounds listed in Table 4. The structure of resulting isothiocyanate-amine derivative of TRITC and 3,4-difluoroaniline is shown in FIG. 6.

The following units of measure have been mentioned in this disclosure:

| Unit of Measure | Full form |
| --- | --- |
| nm | Nanometers |
| Da | Daltons |

In some implementations, a composition includes a functionalized fluorescent dye. The functionalized fluorescent dye includes an isothiocyanate-containing dye functionalized with a functional group that includes a primary amine. The isothiocyanate-containing dye is selected from the group consisting of fluorescein isothiocyanate, Rhodamine B isothiocyanate, or tetramethylrhodamine isothiocyanate, or any isoform thereof. The functional group comprises a primary amine is selected from Group I, Group II, or Group III. Group I consists of ethylamine, propylamine, isopropylamine, butylamine, tert-butylamine, hexylamine, octylamine, decylamine, dodecylamine, tetradecylamine, and hexadecylamine. Group II consists of aniline, benzylamine, phenethylamine, 3-phenyl propylamine, 4-phenylbutylamine, and 6-phenylhexan-1-amine. Group III consists of 4-fluoroaniline, 3,4-difluoroaniline, 2,4,6-trifluoroaniline, 4-(trifluoromethyl)aniline, 3,5-bis(trifluoromethyl)aniline, 2,4,6-tris(trifluoromethyl)aniline, 4-fluoro-3-(trifluoromethyl)aniline, 4-(trifluoromethoxy)aniline, 4-fluorobenzylamine, 2,4-difluorobenzylamine, 2,3,4-trifluorobenzylamine, 3-(trifluoromethyl)benzylamine, and 3,5-bis(trifluoromethyl)benzylamine.

This aspect, taken alone or combinable with any other aspect, can include the following features. The isothiocyanate-containing dye is fluorescein isothiocyanate, and the functional group that includes a primary amine is selected from Group I.

This aspect, taken alone or combinable with any other aspect, can include the following features. The isothiocyanate dye is fluorescein isothiocyanate, and the functional group that includes a primary amine is octylamine.

This aspect, taken alone or combinable with any other aspect, can include the following features. The isothiocyanate-containing dye is fluorescein isothiocyanate, and the functional group that includes a primary amine is selected from Group II.

This aspect, taken alone or combinable with any other aspect, can include the following features. The isothiocyanate-containing dye is fluorescein isothiocyanate, and the functional group that includes a primary amine is selected from Group III.

This aspect, taken alone or combinable with any other aspect, can include the following features. The isothiocyanate-containing dye is Rhodamine B isothiocyanate, and the functional group including a primary amine is selected from Group I.

This aspect, taken alone or combinable with any other aspect, can include the following features. The isothiocyanate-containing dye is Rhodamine B isothiocyanate, and the functional group that includes a primary amine is selected from Group II.

This aspect, taken alone or combinable with any other aspect, can include the following features. The isothiocyanate-containing dye is Rhodamine B isothiocyanate, and the functional group that includes a primary amine is benzylamine.

This aspect, taken alone or combinable with any other aspect, can include the following features. The isothiocyanate-containing dye is Rhodamine B isothiocyanate, and the functional group that includes a primary amine is selected from Group III.

This aspect, taken alone or combinable with any other aspect, can include the following features. The isothiocyanate-containing dye is tetramethylrhodamine isothiocyanate and the functional group that includes a primary amine is selected from Group I.

This aspect, taken alone or combinable with any other aspect, can include the following features. The isothiocyanate-containing dye is tetramethylrhodamine isothiocyanate and the functional group that includes a primary amine is selected from Group II.

This aspect, taken alone or combinable with any other aspect, can include the following features. The isothiocyanate-containing dye is tetramethylrhodamine isothiocyanate and the functional group that includes a primary amine is selected from Group III.

This aspect, taken alone or combinable with any other aspect, can include the following features. The isothiocyanate-containing dye is tetramethylrhodamine isothiocyanate and the functional group that includes a primary amine is 3,4-difluoroaniline.

In some implementations, method of making a functionalized fluorescent dye, includes dissolving a water-soluble isothiocyanate-containing fluorescent dye in an aqueous solvent to yield an aqueous dye solution. The water-soluble isothiocyanate-containing fluorescent dye is selected from the group consisting of fluorescein isothiocyanate, Rhodamine B isothiocyanate, or tetramethylrhodamine isothiocyanate, or any isoform thereof. The method includes dissolving a functional group including a primary amine in an organic solvent to yield an organic functional group solution. The functional group that includes a primary amine is selected from Group I, Group II, or Group III. Group I consists of ethylamine, propylamine, isopropylamine, butylamine, tert-butylamine, hexylamine, octylamine, decylamine, dodecylamine, tetradecylamine, and hexadecylamine. Group II consists of aniline, benzylamine, phenethylamine, 3-phenyl-1-propylamine, 4-phenylbutylamine, and 6-phenylhexan-1-amine. Group III consists of 4-fluoroaniline, 3,4-difluoroaniline, 2,4,6-trifluoroaniline, 4-(trifluoromethyl)aniline, 3,5-bis(trifluoromethyl)aniline, 2,4,6-tris(trifluoromethyl)aniline, 4-fluoro-3-(trifluoromethyl)aniline, 4-(trifluoromethoxy)aniline, 4-fluorobenzylamine, 2,4-difluorobenzylamine, 2,3,4-trifluorobenzylamine, 3-(trifluoromethyl)benzylamine, and 3,5-bis(trifluoromethyl)benzylamine. The method includes forming an emulsion of the aqueous dye solution and the organic functional group solution, and extracting the functionalized fluorescent dye from the organic functional group solution, wherein the functionalized fluorescent dye is a reaction product of the water-soluble isothiocyanate-containing dye and the functional group that includes a primary amine.

This aspect, taken alone or combinable with any other aspect, can include the following features. The aqueous solvent is deionized water.

This aspect, taken alone or combinable with any other aspect, can include the following features. The organic solvent is chloroform.

This aspect, taken alone or combinable with any other aspect, can include the following features. Extracting the functionalized fluorescent dye from the organic functional group solution includes evaporating the organic solvent.

In some implementations, a method of tracing fluid flow in a subterranean formation includes mixing a functionalized fluorescent tracer into a fluid to yield a tracer fluid. The functionalized fluorescent tracer includes an isothiocyanate-containing fluorescent dye functionalized with a functional group that includes a primary amine. The isothiocyanate-containing fluorescent dye is selected from the group consisting of fluorescein isothiocyanate, Rhodamine B isothiocyanate, or tetramethylrhodamine isothiocyanate, or any isoform thereof. The functional group that includes a primary amine is selected from Group I, Group II, or Group III. Group I consists of ethylamine, propylamine, isopropylamine, butylamine, tert-butylamine, hexylamine, octylamine, decylamine, dodecylamine, tetradecylamine, hexadecylamine, and octadecylamine. Group II consists of aniline, benzylamine, phenethylamine, 3-phenyl-1-propylamine, 4-phenylbutlamine, and 6-phenylhexan-1-amine. Group III consists of 4-fluoroaniline, 3,4-difluoroaniline, 2,4,6-trifluoroaniline, 4-(trifluoromethyl)aniline, 3,5-bis(trifluoromethyl)aniline, 2,4,6-tris(trifluoromethyl)aniline, 4-fluoro-3-(trifluoromethyl)aniline, 4-(trifluoromethoxy)aniline, 4-fluorobenzylamine, 2,4-difluorobenzylamine, 2,3,4-trifluorobenzylamine, 3-(trifluoromethyl)benzylamine, and 3,5-bis(trifluoromethyl)benzylamine. The method includes flowing the tracer fluid into a first subterranean formation, recovering a sample from the first subterranean formation or a second subterranean formation, analyzing the sample for a fluorescent signal, and further separating the sample and analyzing the sample for a barcode functional group.

This aspect, taken alone or combinable with any other aspect, can include the following features. The method includes identifying the functionalized fluorescent tracer in the sample using fluorescence, HPLC, LC-MS, or pyrolysis-GC-MS, or any combination thereof.

This aspect, taken alone or combinable with any other aspect, can include the following features. The sample is a fluid sample or a solid sample, and wherein the fluid is a fracking fluid or a drilling mud.

The term "about" as used in this disclosure can allow for a degree of variability in a value or range, for example, within 10%, within 5%, or within 1% of a stated value or of a stated limit of a range.

The term "substantially" as used in this disclosure refers to a majority of, or mostly, as in at least about 50%, 60%, 70%, 80%, 90%, 95%, 96%, 97%, 98%, 99%, 99.5%, 99.9%, 99.99%, or at least about 99.999% or more.

The term "solvent" as used in this disclosure refers to a liquid that can dissolve a solid, another liquid, or a gas to form a solution. Non-limiting examples of solvents are silicones, organic compounds, water, alcohols, ionic liquids, and supercritical fluids.

The term "room temperature" as used in this disclosure refers to a temperature of about 15 degrees Celsius (° C.) to about 28° C.

The term "downhole" as used in this disclosure refers to under the surface of the earth, such as a location within or fluidly connected to a wellbore.

As used in this disclosure, the term "drilling fluid" refers to fluids, slurries, or muds used in drilling operations downhole, such as during the formation of the wellbore.

As used in this disclosure, the term "fluid" refers to liquids and gels, unless otherwise indicated.

As used in this disclosure, the term "subterranean material" or "subterranean zone" or "subterranean formation" refers to any material under the surface of the earth, including under the surface of the bottom of the ocean. For example, a subterranean zone or material can be any section of a wellbore and any section of a subterranean petroleum- or water-producing formation or region in fluid contact with the wellbore. Placing a material in a subterranean zone can include contacting the material with any section of a wellbore or with any subterranean region in fluid contact the material. Subterranean materials can include any materials placed into the wellbore such as cement, drill shafts, liners, tubing, casing, or screens; placing a material in a subterranean zone can include contacting with such subterranean materials. In some examples, a subterranean zone or material can be any downhole region that can produce liquid or gaseous petroleum materials, water, or any downhole section in fluid contact with liquid or gaseous petroleum materials, or water. For example, a subterranean zone or material can be at least one of an area desired to be fractured, a fracture or an area surrounding a fracture, and a flow pathway or an area surrounding a flow pathway, in which a fracture or a flow pathway can be optionally fluidly connected to a subterranean petroleum- or water-producing region, directly or through one or more fractures or flow pathways.

As used in this disclosure, "treatment of a subterranean zone" can include any activity directed to extraction of water or petroleum materials from a subterranean petroleum- or water-producing formation or region, for example, including drilling, stimulation, hydraulic fracturing, clean-up, acidizing, completion, cementing, remedial treatment, abandonment, aquifer remediation, identifying oil rich regions via imaging techniques, and the like.

As used in this disclosure, a "flow pathway" downhole can include any suitable subterranean flow pathway through which two subterranean locations are in fluid connection. The flow pathway can be sufficient for petroleum or water to flow from one subterranean location to the wellbore or vice-versa. A flow pathway can include at least one of a hydraulic fracture, and a fluid connection across a screen, across gravel pack, across proppant, including across resin-bonded proppant or proppant deposited in a fracture, and across sand. A flow pathway can include a natural subterranean passageway through which fluids can flow. In some implementations, a flow pathway can be a water source and can include water. In some implementations, a flow pathway can be a petroleum source and can include petroleum. In some implementations, a flow pathway can be sufficient to divert water, a downhole fluid, or a produced hydrocarbon from a wellbore, fracture, or flow pathway connected to the pathway.

As used in this disclosure, "weight percent" (wt %) can be considered a mass fraction or a mass ratio of a substance to the total mixture or composition. Weight percent can be a weight-to-weight ratio or mass-to-mass ratio, unless indicated otherwise.

A number of implementations of the disclosure have been described. Nevertheless, it will be understood that various modifications may be made without departing from the spirit and scope of the disclosure.

What is claimed is:

1. A composition comprising:
a functionalized fluorescent dye, wherein the functionalized fluorescent dye is formed from an isothiocyanate-containing dye reacted with a primary amine selected from the group consisting of benzylamine, phenethylamine, 3-phenyl-1-propylamine, 4-phenylbutylamine, and 6-phenylhexan-1-amine wherein
the isothiocyanate-containing dye is selected from the group consisting of Rhodamine B isothiocyanate, an isomer thereof, tetramethylrhodamine isothiocyanate, and an isomer thereof.

2. The composition of claim 1, wherein the isothiocyanate-containing dye is Rhodamine B isothiocyanate.

3. The composition of claim 1, wherein the isothiocyanate-containing dye is Rhodamine B isothiocyanate, and the primary amine is benzylamine.

4. The composition of claim 1, wherein the isothiocyanate-containing dye is Rhodamine B isothiocyanate, and the primary amine is phenethylamine.

5. The composition of claim 1, wherein the isothiocyanate-containing dye is Rhodamine B isothiocyanate, and the primary amine is 3-phenyl-1-propylamine.

6. The composition of claim 1, wherein the isothiocyanate-containing dye is Rhodamine B isothiocyanate, and the primary amine is 4-phenylbutylamine.

7. The composition of claim 1, wherein the isothiocyanate-containing dye is Rhodamine B isothiocyanate, and the primary amine is 6-phenylhexan-1-amine.

8. The composition of claim 1, wherein the isothiocyanate-containing dye is tetramethylrhodamine isothiocyanate.

9. The composition of claim 1, wherein the isothiocyanate-containing dye is tetramethylrhodamine isothiocyanate, and the primary amine is benzylamine.

10. The composition of claim 1, wherein the isothiocyanate-containing dye is tetramethylrhodamine isothiocyanate, and the primary amine is phenethylamine.

11. The composition of claim 1, wherein the isothiocyanate-containing dye is tetramethylrhodamine isothiocyanate, and the primary amine is 3-phenyl-1-propylamine.

12. The composition of claim 1, wherein the isothiocyanate-containing dye is tetramethylrhodamine isothiocyanate, and the primary amine is 4-phenylbutylamine.

13. The composition of claim 1, wherein the isothiocyanate-containing dye is tetramethylrhodamine isothiocyanate, and the primary amine is 6-phenylhexan-1-amine.

14. A composition comprising:
a functionalized fluorescent dye, wherein the functionalized fluorescent dye is formed from an isothiocyanate-containing dye reacted with a primary amine selected from the group consisting of 3-phenyl-1-propylamine, 4-phenylbutylamine, and 6-phenylhexan-1-amine wherein
the isothiocyanate-containing dye is fluorescein isothiocyanate, or an isomer thereof.

15. The composition of claim 14, wherein the primary amine is 3-phenyl-1-propylamine.

16. The composition of claim 14, wherein the primary amine is 4-phenylbutylamine.

17. The composition of claim 14, wherein the primary amine is 6-phenylhexan-1-amine.

* * * * *